United States Patent
Davies et al.

(10) Patent No.: US 10,017,828 B2
(45) Date of Patent: Jul. 10, 2018

(54) SYSTEM AND METHOD FOR ANALYSIS OF PLANT MATERIAL FOR A SET OF UNIQUE EXOGENOUS GENETIC ELEMENTS

(71) Applicant: DOW AGROSCIENCES LLC, Indianapolis, IN (US)

(72) Inventors: John P. Davies, Portland, OR (US); Warren S. Lee, Brownsburg, IN (US); Vaka S. Reddy, Aurora, CO (US); Xing Liang Liu, Lake Oswego, OR (US); Satyalinga S. Gampala, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 965 days.

(21) Appl. No.: 14/204,957

(22) Filed: Mar. 11, 2014

(65) Prior Publication Data

US 2014/0287407 A1 Sep. 25, 2014

Related U.S. Application Data

(60) Provisional application No. 61/799,330, filed on Mar. 15, 2013.

(51) Int. Cl.
*C12Q 1/68* (2018.01)
*C12P 19/34* (2006.01)
*C12Q 1/6895* (2018.01)
*C12Q 1/6816* (2018.01)

(52) U.S. Cl.
CPC ........ *C12Q 1/6895* (2013.01); *C12Q 1/6816* (2013.01)

(58) Field of Classification Search
None
See application file for complete search history.

(56) References Cited

U.S. PATENT DOCUMENTS 6,498,286 B1  12/2002  Baluch
7,964,716 B2   6/2011  Liu et al.

2003/0148278 A1   8/2003  Lauter et al.
2006/0281096 A1  12/2006  Chou et al.
2009/0239234 A1   9/2009  Remacle et al.
2010/0120032 A1   5/2010  Van Den Bulcke et al.

FOREIGN PATENT DOCUMENTS

WO  2010070462  6/2010
WO  2011100617  8/2011

OTHER PUBLICATIONS

Prins, Theo W., et al., "Optimised padlock probe ligation and microarray detection of multiple (non-authorized) GMOs in a single reaction," BMC Genomics, Dec. 4, 2008, 12 pages.
Taverniers, Isabel et al., "DNA-based characterization techniques: applications for GMO testing," First Global GMO Conference, Jun. 24-27, 2008, 4 pages.
Broeders, et al, "How to deal with the upcoming challenges in GMO detection in food and feed," Journal of Biomedicine and Biotechnology, 2012, pp. 1-11 ,vol. 2012.
Nadal, A., et al., "A new PCR-CGE (size and color) method for simultaneous detection of genetically modified maize events," Electrophoresis, 2006, pp. 3879-3888, vol. 27, No. 19.
Rudi, K., et al., "A novel multiplex quantitative DNA array based PCR (MQDA-PCR) for quantification of transgenic maize in food and feed," Nucleic Acids Research, 2003, pp. 1-8, vol. 31, No. 11.
International Search Report and Written Opinion for PCT/US2014/023611, dated Jun. 27, 2014.
Holst-Jensen, Arne "Testing for genetically modified organisms (GMOs): past, present and future perspectives," Biotechnology Advances, 2009, pp. 1071-1082, vol. 27.
Peano, C., et al., "Multiplex polymerase chain reaction and ligation detection reaction/universal array technology for the traceability of genetically modified organism in foods," Analytical Biochemistry, 2005, pp. 90-100, vol. 346.
Querci, Maddalena, et al., "New approaches in GMO detection," Anal Bioanal Chem, 2010, pp. 1991-2002, vol. 396.
Tengs, Torstein, et al., "Microarray-based method for detection of unknown genetic modifications," BMC Biotechnology, Dec. 18, 2007, 8 pages.
Morisset, Dany, et al., "Alternative DNA amplifications methods to PCR and their application in GMO detection: a review," Eur Food Res Technol, 2008. pp. 1287-1297, vol. 227.

*Primary Examiner* — Young J Kim
(74) *Attorney, Agent, or Firm* — Marcos P. Rivas; Magleby Cataxinos & Greenwood

(57) ABSTRACT

This disclosure concerns a system and method for detecting heterologous DNA in plant materials.

12 Claims, 11 Drawing Sheets

FIG. 1 ered in a transgenic event (e.g., promoter, reporter gene, terminator) are frequently used in multiple vectors, tracking specific events by these genetic elements becomes challenging.

SYSTEM AND METHOD FOR ANALYSIS OF PLANT MATERIAL FOR A SET OF UNIQUE EXOGENOUS GENETIC ELEMENTS

CROSS-REFERENCE TO RELATED APPLICATION

This application claims the benefit of U.S. Provisional Patent Application Ser. No. 61/799,330, filed Mar. 15, 2013, the disclosure of which is hereby incorporated herein in its entirety by this reference.

FIELD OF THE DISCLOSURE

The present disclosure relates to plant biotechnology. Embodiments of the disclosure relate to the use of unique exogenous genetic elements in a system and method for detecting and tracking transgenic events through production and commercialization of genetically modified plants and products produced therefrom.

BACKGROUND

A genetically modified organism (GMO), such as a genetically-modified plant, is defined at least one transformation event that usually involves the insertion of a heterologous gene construct into the recipient organism. The heterologous gene construct is typically composed of several elements, including at least a gene of interest and regulatory regions for exerting control of gene expression. In addition, the construct may be flanked by DNA sequences from the cloning vector. The majority of genetically-modified plants have been transformed with constructs containing the Cauliflower Mosaic Virus (CaMV) 35S promoter (P-35S) and/or the CaMV 35S terminator (T-35S), or the *Agrobacterium tumefaciens* nopaline synthase terminator (T-Nos). The most commonly used cloning vectors are derived from pBR322, containing a gene coding for resistance to ampicillin (bla) antibiotics, and vectors containing a gene coding for resistance to neomycin/kanamycin (nptll) antibiotics.

Detection of GMOs may be desired for many reasons. For example, qualitative detection may be used to identify unauthorized GMO material or use of such material. Further, detection may be desired to identify safe or unsafe material, or for the certification of purity of identity-preserved material. Quantitative detection may be used to comply with legal or contractually-agreed thresholds of GMO contamination (e.g., when products of high purity are desired as in the case of organic farming or seed lot certification). Detection may also play a role in safety assessment and risk management by allowing tracing of the GMO material. In many of the foregoing applications, high sensitivity is required for the detection method.

The development of effective analytical methods for transgene detection and identification of GMOs that reduce time and associated costs of analysis has been an extremely active area of research for many years. Morriset et al. (2008) Eur. Food Res. Technol. 227:1287-97. Yet, no adequate strategy has been devised that provides adequate detection capabilities for the many heterologous gene constructs and transformation events currently in use. DNA is the analyte of choice for the routine laboratory detection and quantification of GMOs since it can be effectively detected after extraction from seed, feed or even highly processed food samples. Preferred current transgene detection methods detect event-specific elements (e.g., transgene sequences) in transgenic plants. Since most of the generic genetic elements Because of the sensitivity desired for detection assays, DNA is typically first amplified by polymerase chain reaction (PCR) from the sample in such an assay. PCR-based GMO detection methods can be Classified according to their level of specificity. Each category corresponds to the identity of the DNA that is amplified in the PCR reaction: (1) screening targets; (2) gene-specific targets; (3) construct-specific targets; and (4) event-specific targets.

The first category of PCR methods (i.e., amplifying screening targets, for example, the P-35S, T-35S, T-Nos, bla, and ornptll genetic elements) have wide applications for detecting transformed material. Matsuoka et al. (2002) J. Agric. Food Chem. 93:35-8. However, these methods cannot be used to identify the GMO, since the presence of the presence of GMO-derived DNA does not necessarily follow from the presence of the screening target. For example, the source of P-35S or T-35S may be naturally-occurring CaMV. Wolf et al. (2000) Eur. Food Res. Technol. 210:367-72.

The second category of PCR methods (i.e., amplifying a gene of interest, for example, the CryIA gene) are more specific than the first category of methods. Vaitilingom et al. (1999) J. Agric. Food Chem. 47:5261-6. There is greater diversity among the genes of interest than among the available (and commonly used) promoters and terminators, and normally a positive signal for the amplification of a specific transgene implies that GM-derived DNA is present in the sample. However, these methods cannot distinguish between different GMOs that may comprise the same gene of interest, such as an herbicide resistance gene. This failing will become more problematic in the future, as common transgenes are stacked together with others in particular combinations that are characteristic of specific GMOs.

The third category of PCR methods targets (i.e., amplifying a junction between adjacent elements of the heterologous gene construct, for example, between the promoter and the gene of interest) provides the only unique signature of a transformation event, within the limitations of present day technology. Zimmerman et al. (1998) Lebensm.-Wiss u Technol. 31: 664-7. Unfortunately, even event-specific methods have their limitations. For example, when two GMOs are crossed (e.g., two different GM maize, such as T25 and Mon810), the resulting hybrid offspring may contain signatures of both events and will therefore be indistinguishable from its two parents in a PCR test. A further onerous limitation of these detection methods is that a specific primer pair is required for each GMO to identify. Moreover, information regarding the construct insertion site is necessary to design primers and conduct the detection assay, which makes detection of uncharacterized GMOs impossible.

New approaches adhere to a general strategy including the selection of an optimal set of different detection methods to search for and identify particular GMOs present in a sample. Querci et al. (2010) Anal. Bioanal. Chem. 396:1991-2002. Recently, a database providing information on optimal detection methods for particular GMOs, and including specific DNA sequences of inserted and flanking elements in many of the GMOs, was provided. Dong et al. (2008) BMC Bioinformatics 9:260. The database is to be updated and increased as new GMOs are introduced and detection methods investigated as a collective task for entities involved in the detection of GMOs. This database is expected to be a useful tool for analytical laboratories performing GMO testing.

In the future, however, GMO detection according to this conventional wisdom will become prohibitively expensive, due to increasing numbers of approved GMO plants, each of which will have its own optimal detection method. Furthermore, it is increasingly common to combine multiple agronomic traits in a single GMO ("gene stacking"). Taverniers et al. (2008) Environ. Biosafety Res. 7:197-218. Gene stacking introduces a difficult challenge to GMO detection. With the exception of testing of single seeds or tissue derived from individual plants, no existing detection method can adequately discriminate between the combined presence of material from two or more single trait GMOs, and single stacked GMOs. Akiyama et al. (2005) J. Agric. Food Chem. 55:5942-7; Holst-Jensen et al. (2006) J. Agric. Food Chem. 54:2799-809; Taverniers et al. (2008), supra.

In recent years, DNA-based detection methods including microarray/chip and multiplex PCRs were explored for the potential for increasing detection assay sensitivity and output, and for identifying stacked GMOs. See, e.g., Tengs et al. (2007) BMC Biotechnol. 7:91. For example, Peano et al. (2005) Anal. Biochem. 346:90-100 and Prins et al. (2008) BMC Genomics 9:584 reported an approach combining a transgene specific ligation reaction, PCR amplification of the ligated oligonucleotide, hybridization, and microarray detection. Multiple oligonucleotide tags immobilized on the microarray surface that targeted the amplified ligation products were used to provide multiplex capabilities in this approach. Such detection methods and multiplexing tools represent the approaches currently used to develop GMO detection methods that address the expectation that sensitive detection will be required in the future from complicated samples containing a diverse plurality of events.

BRIEF SUMMARY OF THE DISCLOSURE

Described herein is a system providing a single highly-specific and highly-sensitive PCR-based detection assay for determining the presence of a plurality of unique transgenic events. In some embodiments, the system and method thereof does not require any information regarding the integration site of the transgenic event to perform the method. In some examples, a single pair of oligonucleotide primers (a universal primer pair) may be utilized to amplify polynucleotides from many different exogenous constructs that may then be specifically detected via a single assay. Embodiments herein utilize unique nucleotide sequences (within a set of vectors) that may have similar thermodynamic properties, which sequences (referred to in some places herein as "unique exogenous genetic elements" or "UGEs") are uniquely associated with a particular transgene and may be detected in substantially the same assay as other such unique nucleotides within the set of vectors. Systems and methods herein may provide a single means to detect/screen for multiple transgenes, thus reducing the overall number of detection assays required for adventitious presence testing.

Some embodiments provide methods for identifying a heterologous nucleic acid in a plant or plant material (e.g., seed), wherein the heterologous nucleic acid comprises a 5' polynucleotide, a UGE, and a 3' polynucleotide. In particular embodiments, such a method comprises providing a sample comprising DNA from the plant or plant material; contacting the DNA with a pair of oligonucleotide primers that specifically hybridize to the 5' and 3' polynucleotides; amplifying an amplicon comprising the 5' polynucleotide, the UGE, and the 3' polynucleotide; and detecting the UGE using a specific probe (e.g., in a fluorescence-based PCR assay, such as a hydrolysis probe assay). In particular embodiments, such a method comprises detecting the UGE by sequencing the amplified fragments comprising the 5' polynucleotide, the UGE, and the 3' polynucleotide. As demonstrated by the several Examples herein, methods according to particular embodiments provide surprising specificity that is unprecedented in a generalizable GMO detection method.

Some embodiments provide systems for detecting at least one heterologous nucleic acid in a plant or plant material. Some systems comprise a set of vectors each comprising a heterologous nucleic acid containing a 5' polynucleotide, a UGE, and a 3' polynucleotide, wherein the 5' polynucleotide and 3' polynucleotide are universal (i.e., common to all) in the vector set, and wherein the UGE of each of the vectors is unique to the set. Some systems may comprise a universal forward primer oligonucleotide that specifically hybridizes to the 5' polynucleotide, and a universal reverse primer oligonucleotide that specifically hybridizes to the 3' polynucleotide. Particular systems may comprise a set of probe molecules, wherein each of the probe molecules specifically hybridizes to only one of the UGEs in the vector set.

Systems and methods herein may be used to identify the presence of a vast number of transgenic events in GMO plants, including those with stacked transgenes, with a previously unavailable level of specificity and generalizability. In some examples, systems and methods herein obviate the need to independently develop detection assays for different events and combine disparate detection methods to obtain good GMO coverage, which can be a prohibitively expensive strategy.

Multiple genes of interest may be introduced into plant transformation vectors comprising UGEs and universal primer sites, and transgenic plants may be obtained using these vectors. Thereby, multiple genes may be transformed and tracked in transgenic plants using a single UGE-specific detection assay. Transgenic plants transformed with these constructs may be tested using a bulked segregate analysis approach that significantly reduces the number of assays required to identify the transgenic plants for further uses, compared to previously available techniques. Further, systems and methods herein may aid commercial advancement decisions in trait introgression programs by facilitating analysis of field samples for the presence of intended traits, as well as the absence of unintended traits (adventitious presence).

The foregoing and other features will become more apparent from the following detailed description of several embodiments, which proceeds with reference to the accompanying figures.

BRIEF DESCRIPTION OF THE FIGURES

FIG. 1 includes a schematic presentation of a sequence alignment between six exemplary UGE-containing polynucleotides (SEQ ID NOs:55-60), from plasmids pEPP1135-pEPP1140, respectively. F-Primer and R-Primer represent universal forward and reverse PCR primers.

SEQUENCE LISTING

Figure 2:
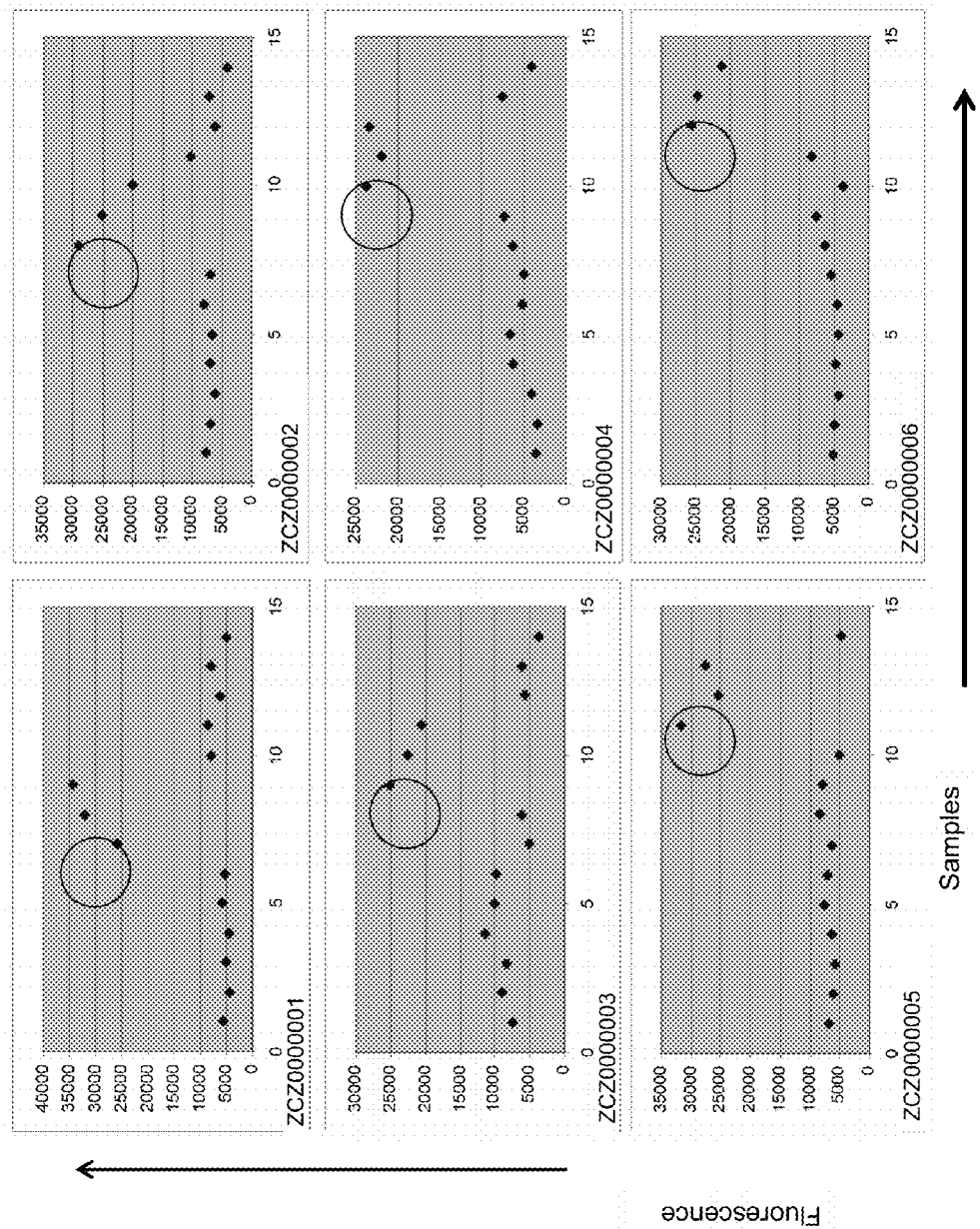
FIG. 2 includes detection results from UGE-specific PCR assays. UGE-specific plasmid DNA were used as the positive controls (shown in circles) and non-transgenic corn DNA and no template control samples were used as negative controls. Samples were run in triplicates.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. In the accompanying sequence listing:

SEQ ID NOs:1-21 show exemplary oligonucleotide probes designed to specifically hybridize to (identical) UGE polynucleotides ("UGE1"-"UGE21," respectively)

SEQ ID NOs:22-42 show amplicons ("Amplicons 1-21"), each comprising an exemplary UGE and 5' and 3' binding sites for universal PCR Forward and Reverse primers.

SEQ ID NOs:43-46 show primers useful in certain UGE fluorescence-based PCR assays to generate amplicons for UGE detection via a hydrolysis probe assay.

SEQ ID NO:47 shows a maize invertase gene that may be used as a positive control in particular embodiments to validate PCR and hydrolysis probe reaction conditions.

SEQ ID NO:48 shows a maize ZSSIIb gene that may be used as a positive control in particular embodiments to validate PCR and hydrolysis probe reaction conditions.

SEQ ID NOs:49-50 show primers useful for amplifying a portion of a maize invertase gene.

SEQ ID NO:51 shows a probe oligonucleotide that may be used to detect a maize invertase gene.

SEQ ID NOs:52-53 show primers useful for amplifying a portion of a maize ZSSIIb gene.

SEQ ID NO:54 shows a probe oligonucleotide that may be used to detect a maize ZSSIIb gene.

SEQ ID NOs:55-60 show UGE-containing polynucleotides from members of a set of plant transformation vectors (pEPP1135-pEPP1140).

DETAILED DESCRIPTION

I. Overview of Several Embodiments

Sensitive and reliable detection methods are necessary for monitoring genetically modified organisms (GMO). Existing DNA detection methods are geared towards targeting the screening elements, plant-specific elements, or event-specific elements in transgenic plants. Described herein is the use of unique, synthetic non-coding synthetic DNA sequences (UGEs) that, when incorporated into plant transformation vectors, may assist in monitoring transgenic plants by serving as targets for robust universal assay development. Several UGE sequences have been tested for the ease of fluorescence-based assay development and their utility in monitoring the transgenic plants was demonstrated. Constructs comprising a UGE flanked by universal primer sites were introduced into plant transformation vectors, and specific hydrolysis probe detection assays were shown to rapidly track each transformation vector.

II. Abbreviations

ABC-transporter ATP-binding cassette transporter
AP adventitious presence
BHQ2 Black Hole Quencher™-2
FAM 6-carboxy fluorescein amidite
FET fluorescent energy transfer
HEX hexachloro-fluorescein
MGBNFQ Minor Groove Binder Non-Fluorescent Quencher
PCR polymerase chain reaction
UGE unique exogenous genetic element III. Terms Adventitious Presence: As used herein, "Adventitious Presence" (AP) refers to the unintentional and incidental commingling of trace amounts of transgenic material in a sample of plant material. Adventitious presence may be exemplified, for example, by the presence of trace amounts of transgenic material in a sample believed to be wholly comprised of non-transgenic material, or may be exemplified by the presence trace amounts of transgenic material of one type in a sample of material believed to be wholly comprised of transgenic material of a different type.

Backcrossing: Backcrossing methods may be used to introduce a nucleic acid sequence into plants. The backcrossing technique has been widely used for decades to introduce new traits into plants. Jensen, N., Ed. Plant Breeding Methodology, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule," as used herein, is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Exogenous: The term "exogenous," as applied to nucleic acids (e.g., polynucleotides, DNA, RNA, and genes) herein, refers to one or more nucleic acid(s) that are not normally present within their specific environment or context. For example, if a host cell is transformed with a nucleic acid that does not occur in the untransformed host cell in nature, then that nucleic acid is exogenous to the host cell. The term exogenous, as used herein, also refers to one or more nucleic acid(s) that are identical in sequence to a nucleic acid already present in a host cell, but that are located in a different cellular or genomic context than the nucleic acid with the same sequence already present in the host cell. For example, a nucleic acid that is integrated in the genome of the host cell in a different location than a nucleic acid with the same sequence is normally integrated in the genome of the host cell is exogenous to the host cell. Furthermore, a nucleic acid (e.g., a DNA molecule) that is present in a plasmid or vector in the host cell is exogenous to the host cell when a nucleic acid with the same sequence is only normally present in the genome of the host cell.

Heterologous: The term "heterologous," as applied to nucleic acids (e.g., polynucleotides, DNA, RNA, and genes) herein, means of different origin. For example, if a host cell is transformed with a nucleic acid that does not occur in the untransformed host cell in nature, then that nucleic acid is heterologous (and exogenous) to the host cell. Furthermore, different elements (e.g., promoter, enhancer, coding sequence, terminator, etc.) of a transforming nucleic acid may be heterologous to one another and/or to the transformed host. The term heterologous, as used herein, may also be applied to one or more nucleic acid(s) that are identical in sequence to a nucleic acid already present in a host cell, but that are now linked to different additional sequences and/or are present at a different copy number, etc.

Sequence identity: The term "sequence identity" or "identity," as used herein, in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "substantially identical" may refer to nucleotide sequences that are more than 85% identical. For example, a substantially identical nucleotide sequence may be at least 85.5%; at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

Probe: In some embodiments, the presence of a particular nucleic acid (e.g., a UGE) in a sample may be detected through the use of a nucleic acid probe. A probe may be a DNA molecule or an RNA molecule. A probe may contain all or a portion of the nucleotide sequence of the particular nucleic acid, and may optionally further contain at least one additional nucleotide sequence and/or label(s).

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: Radiolabeling by nick translation; random priming; tailing with terminal deoxytransferase; etc., where the nucleotides employed are labeled, for example, with radioactive $^{32}$P. Other labels which may be used include, for example and without limitation: Fluorophores (e.g., alone or with a quencher); enzymes; enzyme substrates; enzyme cofactors; enzyme inhibitors; etc. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may also be a nucleic acid molecule that is "specifically hybridizable" or "specifically complementary" to the particular nucleic acid to be detected (i.e., the target). "Specifically hybridizable" and "specifically complementary" are terms that indicate a sufficient degree of complementarity such that stable and specific binding occurs between the probe and the target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ and/or Mg$^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2$^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 µg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

Operably linked: A first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

Promoter: A region of DNA that generally is located upstream (towards the 5' region of a gene) that is needed for transcription. Promoters permit the proper activation or repression of the gene which they control. A promoter contains specific sequences that are recognized by transcription factors. These factors bind to the promoter DNA sequences and result in the recruitment of RNA polymerase, the enzyme that synthesizes the RNA from the coding region of the gene. In some embodiments, tissue-specific promoters are used. A tissue-specific promoter is a DNA sequence that directs a higher level of transcription of an associated gene in the tissue for which the promoter is specific relative to the other tissues of the organism. Examples of tissue-specific promoters include tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Application No. 2001/047525 A1); fruit-specific promoters (See, e.g., U.S. Pat. Nos. 4,943,674, and 5,753,475); and seed-specific promoters (See, e.g., U.S. Pat. Nos. 5,420, 034, and 5,608,152). In some embodiments, developmental stage-specific promoters are also used, e.g., a promoter active at a later stage in development.

Transformed: A virus or vector "transforms" or "transduces" a cell when it transfers nucleic acid molecules into the cell. A cell is "transformed" by a nucleic acid molecule transduced into the cell when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into such a cell. Examples include, but are not limited to, transfection with viral vectors, transformation with plasmid vectors, electroporation (Fromm et al. (1986) Nature 319:791-3), lipofection (Feigner et al. (1987) Proc. Natl. Acad. Sci. USA 84:7413-7), microinjection (Mueller et al. (1978) Cell 15:579-85), *Agrobacterium*-mediated transfer (Fraley et al. (1983) Proc. Natl. Acad. Sci. USA 80:4803-7), direct DNA uptake, and microprojectile bombardment (Klein et al. (1987) Nature 327:70).

Transgene: An exogenous nucleic acid sequence. In one example, a transgene is a gene sequence (e.g., a herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter).

Vector: As used herein, the term "vector" refers to a polynucleotide or other molecule that is capable of transferring at least one nucleic acid segment(s) into a cell. A vector may optionally comprise components/elements that mediate vector maintenance and/or enable its intended use (e.g., sequences necessary for replication, genes imparting drug or antibiotic resistance, a multiple cloning site, and/or operably linked promoter/enhancer elements that enable the expression of a cloned gene). Vectors may be derived, for example, from plasmids, bacteriophages, or plant or animal viruses. A "cloning vector," "shuttle vector," or "subcloning vector" generally comprises operably linked elements to facilitate cloning or subcloning steps (e.g., a multiple cloning site containing multiple restriction endonuclease sites).

Expression Vector: The term "expression vector," as used herein, refers to a vector comprising operably linked polynucleotide sequences that may facilitate expression of a coding sequence in a particular host organism. For example, a bacterial expression vector may facilitate expression of a coding sequence in a bacterium. Likewise, a plant expression vector may facilitate expression of a coding sequence in a plant cell. Polynucleotide sequences that facilitate expression in prokaryotes may include, for example and without limitation, a promoter; an operator; and a ribosome binding site. Eukaryotic expression vectors (e.g., a plant expression vector) may comprise, for example, promoters; enhancers; termination signals; and polyadenylation signals (and other sequences) that are generally different from those used in prokaryotic expression vectors.

Trait or phenotype: The terms "trait" and "phenotype" are used interchangeably herein. For the purposes of the present disclosure, traits of particular interest include agronomically important traits, as may be expressed, for example, in a crop plant.

Unique exogenous genetic element (UGE): UGEs are unique, synthetic DNA sequences that when incorporated into plant transformation vectors, serve as targets for DNA detection assays. First, a single unique pre-validated UGE is introduced into a plant transformation vector. Second, the UGE-containing plant transformation vector is used for cloning multiple genes driven by the same promoter. UGE-specific fluorescence-based PCR assays are rapidly developed to track each transformation vector with relative ease. Transgenic plants derived from these constructs can be tested using a bulked segregate analysis approach to reduce the number of assays significantly.

IV. Unique Exogenous Genetic Elements

Embodiments herein include unique, synthetic non-coding synthetic DNA sequences (referred to herein as "Unique exogenous Genetic Elements," or "UGEs") that may be used to develop a universal method for the UGE-specific detection of nucleic acids. UGEs may be designed such that all of those in a set have similar thermodynamic properties as oligonucleotides in a hybridization assay. Within a set of nucleic acids, for example, for introduction into an organism, a set of distinct/unique UGEs may be included with a further nucleic acid(s) of interest in the nucleic acids of the set, to identify in a specifically identifiable fashion constructs from a particular company or laboratory, constructs containing certain classes of genes or genetic elements, and/or GMOs (e.g., plants) comprising such constructs.

In some embodiments, the UGEs are unique identification markers that are flanked and amplified by common primers, universal to the set, such that nucleic acids comprising the UGEs may be universally and specifically identified, for example, by DNA sequence analysis, hybridization, and fluorescence-based PCR analysis. In some examples, heterologous nucleic acids comprising UGEs in a GMO may be identified using a fluorescence-based real-time PCR method with unique quenchable fluorescently-labeled probes (e.g., a hydrolysis probe) that specifically hybridize to the UGEs. For example, the UGE oligonucleotides themselves may be incorporated in a labeled probe molecule. Universal PCR primers and UGEs may provide highly specific and highly efficient amplification and fluorescence-based detection in a single assay for a complicated GMO material comprising many different transgenes. In some examples, heterologous nucleic acids comprising a UGE in a GMO may be identified by sequencing an amplified DNA fragment that is flanked by the universal primers, so as to determine the identity of the UGE present in the sample.

Fluorescence-coupled PCR is utilized as a detection assay in particular embodiments. Such PCR-based assays are known in the art. U.S. Pat. Nos. 5,210,015 and 5,487,972. For example, particular embodiments utilize a PCR reaction involving three oligonucleotides: a forward primer; a reverse primer; and a fluorogenic probe. The fluorogenic probe may comprise, for example and without limitation, an oligonucleotide labeled at the 5' end with a reporter fluorescent dye (e.g., FAM and HEX), and labeled at the 3' end with a quencher dye (e.g., MGBNFQ and BHQ2). In such exemplary probe molecules, excitation of the reporter fluorescent dye at a specific wavelength (488 nm) will not lead to fluorescence, due to FET suppression as a result of spatial proximity to the quencher dye. During a hydrolysis probe PCR assay, the probe with the primers initially hybridizes to the target DNA. In the extension phase, the probe positioned between the primers contacts the polymerase and is hydrolyzed through its exonuclease activity. Probe hydrolysis releases the fluorescent reporter from the FET suppression, and the reporter fluorescence increases with each PCR cycle in accordance with the accumulation of PCR product.

In some embodiments, a UGE is designed to have a length sufficient to provide adequate sequence diversity within the set comprising the UGE, such that oligonucleotide probes may be designed to specifically hybridize to each of the UGEs in the set. For example, a UGE may be designed to be, for example and without limitation: more than about 10; more than about 15; more than about 20; more than about 25; between about 10 and about 25; between about 15 and about 25; between about 10 and about 20; and between about 15 and about 20 nucleotides in length. In particular embodiments, a UGE is selected from the group consisting of UGE1-UGE21 (SEQ ID NOs:1-21).

In some embodiments, a UGE may be comprised in an amplifiable nucleic acid (an amplicon) that also comprises flanking universal primers. In some examples, the flanking universal primers may be directly adjacent to the UGE; i.e., not separated by any further nucleotide sequence. An amplicon comprising a UGE and flanking universal primers may be of sufficient length to be amplifiable in a PCR reaction. For example and without limitation, such an amplicon may be less than about 150; less than about 130; less than about 110; less than about 100; less than about 90; less than about 85; less than about 80; between about 60 and about 100; between about 60 and about 90; between about 60 and about 80; between about 70 and about 100; between about 70 and about 90; and between about 70 and about 80 nucleotides in length. In particular embodiments, an amplicon comprising a UGE and flanking primer sites is selected from the group consisting of Amplicons 1-21 (SEQ ID NOs:22-42).

In some embodiments, a UGE (e.g., in an amplicon also comprising flanking universal primers) may, for example, be comprised in a vector system including, for example and without limitation, a linear plasmid, and a closed circular plasmid. In particular examples, the vector may be an expression vector. Amplicons comprising UGEs according to particular embodiments may, for example, be inserted into a vector, such that the nucleic acid sequence is operably linked to one or more regulatory sequences. Many vectors are available for this purpose, and selection of the particular vector may depend, for example, on the size of the nucleic acid to be inserted into the vector, the particular host cell to be transformed with the vector, and/or the amount of the fusion protein that is desired to be expressed. A vector typically contains various components, the identity of which depend on a function of the vector (e.g., amplification of DNA and expression of DNA), and the particular host cell(s) with which the vector is compatible.

Some embodiments may include a plant transformation vector that comprises a UGE flanked by universal primer sites, and a gene of interest that is operatively linked to at least one regulatory sequence. The gene of interest may be expressed, under the control of the regulatory sequence(s), in a plant cell, tissue, or organism to produce the fusion protein. Such a regulatory sequence may be a promoter sequence that functions in a host plant cell.

Promoters suitable for use in nucleic acid molecules according to some embodiments include those that are inducible, viral, synthetic, or constitutive, all of which are well known in the art. Non-limiting examples of promoters that may be useful in embodiments of the invention are provided by: U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. patent application Ser. No. 09/757,089 (maize chloroplast aldolase promoter).

Additional exemplary promoters include the nopaline synthase (NOS) promoter (Ebert et al. (1987) Proc. Natl. Acad. Sci. USA 84(16):5745-9); the octopine synthase (OCS) promoter (which is carried on tumor-inducing plasmids of *Agrobacterium tumefaciens*); the cauliomovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV35S (U.S. Pat. Nos. 5,322,938, 5,352,605, 5,359,142, and 5,530,196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) J. Mol. Appl. Genet. 1:561-73; Bevan et al. (1983) Nature 304:184-7).

In particular embodiments, nucleic acid molecules of the invention may comprise a tissue-specific promoter. A tissue-specific promoter is a nucleotide sequence that directs a higher level of transcription of an operably linked nucleotide sequence in the tissue for which the promoter is specific, relative to the other tissues of the organism. Examples of tissue-specific promoters include, without limitation: tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Application No. 2001/047525 A1); fruit-specific promoters (See, e.g., U.S. Pat. Nos. 4,943,674, and 5,753,475); and seed-specific promoters (See, e.g., U.S. Pat. Nos. 5,420,034, and 5,608,152). In some embodiments, a developmental stage-specific promoter (e.g., a promoter active at a later stage in development) may be used in a composition or method of the invention.

Additional regulatory sequences that may in some embodiments be operably linked to a nucleic acid molecule include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5' UTRs are provided by: GmHsp (U.S. Pat. No. 5,659,122); PhDnaK (U.S. Pat. No. 5,362,865); AtAnt1; TEV (Carrington and Freed (1990) J. Virol. 64:1590-7); and AGRtunos (GenBank Accession No. V00087; and Bevan et al. (1983), supra).

Additional regulatory sequences that may in some embodiments be operably linked to a nucleic acid molecule also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al. (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank Accession No. E01312).

Additional information regarding regulatory sequences that may be useful in particular embodiments is described, for example, in Goeddel (1990) "Gene Expression Technology," Methods Enzymol. 185, Academic Press, San Diego, Calif.

A recombinant nucleic acid molecule or vector of the present invention may comprise a selectable marker that confers a selectable phenotype on a transformed cell, such as a plant cell. Selectable markers may also be used to select for plants or plant cells that comprise a nucleic acid molecule of the invention. The marker may encode biocide resistance, antibiotic resistance (e.g., kanamycin, Geneticin (G418), bleomycin, and hygromycin), or herbicide resistance (e.g., glyphosate). Examples of selectable markers include, but are not limited to: a neo gene that confers kanamycin resistance and can be selected for using, e.g., kanamycin and G418; a bar gene that confers bialaphos resistance; a mutant EPSP synthase gene that confers glyphosate resistance; a nitrilase gene that confers resistance to bromoxynil; a mutant acetolactate synthase gene (ALS) that confers imidazolinone or sulfonylurea resistance; and a methotrexate-resistant DHFR gene. Multiple selectable markers are available that confer resistance to chemical agents including, for example and without limitation, ampicillin; bleomycin; chloramphenicol; gentamycin; hygromycin; kanamycin; lincomycin; methotrexate; phosphinothricin; puromycin; spectinomycin; rifampicin; streptomycin; and tetracycline. Examples of such selectable markers are illustrated in, e.g., U.S. Pat. Nos. 5,550,318; 5,633,435; 5,780,708 and 6,118,047.

A nucleic acid molecule or vector of the present invention may also or alternatively include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In *18th Stadler Genetics Symposium*, P. Gustafson and R. Appels, eds., Plenum, N.Y. (pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); a xylE gene that encodes a catechol dioxygenase that converts chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone, which in turn condenses to melanin (Katz et al. (1983) J. Gen. Microbiol. 129:2703-14); and an α-galactosidase.

Suitable methods for transformation of host cells include any method by which DNA can be introduced into a cell, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); and by acceleration of DNA-coated particles (See, e.g., U.S. Pat. Nos. 5,015,580, 5,550,318, 5,538,880, 6,160,208, 6,399,861, and 6,403,865). Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences of the invention in the genome of the transgenic plant.

The most widely-utilized method for introducing an expression vector into plants is based on the natural transformation system of *Agrobacterium*. *A. tumefaciens* and *A. rhizogenes* are plant pathogenic soil bacteria that genetically transform plant cells. The $T_i$ and $R_i$ plasmids of *A. tumefaciens* and *A. rhizogenes*, respectively, carry genes responsible for genetic transformation of the plant. The $T_i$(tumor-inducing)-plasmids contain a large segment, known as T-DNA, which is transferred to transformed plants. Another segment of the $T_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the invention.

Thus, in some embodiments, a plant transformation vector is derived from a $T_i$ plasmid of *A. tumefaciens* (See, e.g., U.S. Pat. Nos. 4,536,475, 4,693,977, 4,886,937, and 5,501,967; and European Patent EP 0 122 791) or a $R_i$ plasmid of *A. rhizogenes*. Additional plant transformation vectors include, for example and without limitation, those described by Herrera-Estrella et al. (1983) Nature 303:209-13; Bevan et al. (1983), supra; Klee et al. (1985) Bio/Technol. 3:637-42; and in European Patent EP 0 120 516, and those derived from any of the foregoing. Other bacteria, such as *Sinorhizobium*, *Rhizobium*, and *Mesorhizobium* that naturally interact with plants can be modified to mediate gene transfer to a number of diverse plants. These plant-associated symbiotic bacteria can be made competent for gene transfer by acquisition of both a disarmed $T_i$ plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

A transgenic plant formed using *Agrobacterium*-dependent transformation methods typically contains a single recombinant DNA sequence inserted into one chromosome. The single recombinant DNA sequence is referred to as a "transgenic event" or "integration event." Such transgenic plants are heterozygous for the inserted DNA sequence. In some embodiments, a transgenic plant homozygous with respect to a transgene may be obtained by sexually mating (selfing) an independent segregant transgenic plant that contains a single exogenous gene sequence to itself, for example, an $F_0$ plant, to produce $F_1$ seed. One fourth of the $F_1$ seed produced will be homozygous with respect to the transgene. Germinating $F_1$ seed results in plants that can be tested for heterozygosity, typically using a SNP assay or a thermal amplification assay that allows for the distinction between heterozygotes and homozygotes (i.e., a zygosity assay).

In addition to direct transformation of a plant or plant cell with a nucleic acid molecule of the invention, transgenic plants may be prepared in some embodiments by crossing a first plant having at least one transgenic event with a second plant lacking such an event. For example, a nucleic acid molecule comprising a UGE may be introduced into a first plant line that is amenable to transformation, to produce a transgenic plant, which transgenic plant may be crossed with a second plant line to introgress the nucleic acid molecule comprising the UGE into the second plant line.

In some embodiments herein, any GMO may be analyzed. In particular embodiments, the GMO is a genetically-modified plant. A plant material sample that is analyzed using particular systems and methods herein may be any substance that can comprise different and multiple exogenous nucleic acids, for example and without limitation, exogenous nucleic acids that are specific to a genetically modified plant, or having a genetically modified plant origin. In some examples, a sample may be a food, a food ingredient, a food additive, and/or a solid or liquid extract that could comprise material from a GMO. In some examples, nucleic acids may be extracted from the plant material sample prior to analysis.

Genetically modified plants may be a dicot or monocot plant species. Non-limiting examples of plant cells from dicotyledonous plants that may be analyzed according to specific embodiments the invention include: alfalfa; beans; *Brassica*; broccoli; cabbage; canola; carrot; cauliflower; celery; Chinese cabbage; cotton; cucumber; eggplant; lettuce; melon; pea; pepper; peanut; potato; pumpkin; radish; rapeseed; spinach; soybean; squash; sugarbeet; sunflower; tobacco; tomato; and watermelon. Non-limiting examples of plant cells from monocotyledonous plants that may be transformed according to specific embodiments the invention include: maize; onion; rice; sorghum; wheat; rye; millet; sugarcane; oat; triticale; switchgrass; and turfgrass.

The following examples are provided to illustrate certain particular features and/or embodiments. The examples should not be construed to limit the disclosure to the particular features or embodiments exemplified.

EXAMPLES

Example 1: Design and Construction of Vectors Comprising Unique Genetic Elements for Transgenic Plant Production Unique, synthetic genetic elements (UGEs) comprising random nucleotide sequences of 15-25 bp were generated using a macro in the Excel® (MICROSOFT) application. A random number series was generated of the desired length comprising digits 1 through 4. Each digit was matched to a specified nucleotide base (e.g., 1=A; 2=C; 3=G; and 4=T) to generate a polynucleotide that was then synthesized by a commercial vendor for cloning manipulations.

The UGEs were each incorporated into a 70-80 bp longer sequence (referred to herein as an amplicon) comprising flanking sequences for binding of universal PCR Forward and Reverse primers. 21 UGEs and 21 related amplicons (each comprising a UGE sequence and flanking universal primer binding sites) were designed and were synthesized into high copy plasmids by a commercial vendor (DNA 2.0; Menlo Park, Calif.). Table 1 lists the sequences of 21 UGEs and the corresponding amplicons.

TABLE 1

Sequences of UGEs and of amplicons comprising a specific UGE (underlined) and universal primer binding sites

| UGE No. | UGE Sequence | Amplicon Sequence |
|---|---|---|
| 1 | TTCAATTCTGGA AATCC (SEQ ID NO: 1) | TGCAGGTCAATCCCATTGCTTTTGTTCAATTCTGGAAATC CTCTCTGCGATCGCTTCTCGAGGTCATTCATATGCTTG (SEQ ID NO: 22) |

TABLE 1-continued

Sequences of UGEs and of amplicons comprising a specific UGE (underlined) and universal primer binding sites

| UGE No. | UGE Sequence | Amplicon Sequence |
|---|---|---|
| 2 | AACAAAGGCCCC AATC (SEQ ID NO: 2) | TGCAGGTCAATCCCATTGCTTTTG<u>AACAAAGGCCCCAATC</u>TCTCTGCGATCGCTTCTCGAGGTCATTCATATGCTTG (SEQ ID NO: 23) |
| 3 | CACCTACCCACC CTACT (SEQ ID NO: 3) | TGCAGGTCAATCCCATTGCTTTTG<u>CACCTACCCACCCTACT</u>TCTCTGCGATCGCTTCTCGAGGTCATTCATATGCTTG (SEQ ID NO: 24) |
| 4 | CGTTATCCCGCA TAGTAG (SEQ ID NO: 4) | TGCAGGTCAATCCCATTGCTTTTG<u>CGTTATCCCGCATAGTAGT</u>CTCTGCGATCGCTTCTCGAGGTCATTCATATGCTTG (SEQ ID NO: 25) |
| 5 | ATTGGTTTGGTG GTGAGAT (SEQ ID NO: 5) | TGCAGGTCAATCCCATTGCTTTTG<u>ATTGGTTTGGTGGTGAGAT</u>TCTCTGCGATCGCTTCTCGAGGTCATTCATATGCTTG (SEQ ID NO: 26) |
| 6 | ACGTATCACAGC TCCTAG (SEQ ID NO: 6) | TGCAGGTCAATCCCATTGCTTTTG<u>ACGTATCACAGCTCCTAGT</u>CTCTGCGATCGCTTCTCGAGGTCATTCATATGCTTG (SEQ ID NO: 27) |
| 7 | TTAGTATTGGCA GCAGACC (SEQ ID NO: 7) | GGCGCCCGGTATTTGTTAAAAGCGG<u>CTACTTAGTATTGGCAGCAGACC</u>TAGTCAAGACGAGCAGTCCGAAGCGATCGC (SEQ ID NO: 28) |
| 8 | CCAATAAGACTG AAGTTGAC (SEQ ID NO: 8) | GGCGCCCGGTATTTGTTAAAAGCGG<u>CCAATAAGACTGAAGTTGAC</u>TAGTCAAGACGAGCAGTCCGAAGCGATCGC (SEQ ID NO: 29) |
| 9 | CTACCTCGATCG CCCATA (SEQ ID NO: 9) | GGCGCCCGGTATTTGTTAAAAGCGG<u>CTACCTCGATCGCCCATA</u>TAGTCAAGACGAGCAGTCCGAAGCGATCGC (SEQ ID NO: 30) |
| 10 | TGTTAGGCTACG ATAGGGTT (SEQ ID NO: 10) | GGCGCCCGGTATTTGTTAAAAGCGG<u>TGTTAGGCTACGATAGGGTT</u>TAGTCAAGACGAGCAGTCCGAAGCGATCGC (SEQ ID NO: 31) |
| 11 | TACGCGCTTCAT CCTA (SEQ ID NO: 11) | GGCGCCCGGTATTTGTTAAAAGCGG<u>TACGCGCTTCATCCTA</u>TAGTCAAGACGAGCAGTCCGAAGCGATCGC (SEQ ID NO: 32) |
| 12 | CGACTCATCAAA CACGATT (SEQ ID NO: 12) | GGCGCCCGGTATTTGTTAAAAGCGG<u>CGACTCATCAAACACGATT</u>TAGTCAAGACGAGCAGTCCGAAGCGATCGC (SEQ ID NO: 33) |
| 13 | ACAATTCTCACT TTCGTCTAT (SEQ ID NO: 13) | GGCGCCCGGTATTTGTTAAAAGCGG<u>ACAATTCTCACTTTCGTCTAT</u>TAGTCAAGACGAGCAGTCCGAAGCGATCGC (SEQ ID NO: 34) |
| 14 | CACCCGCATCAT GTAGA (SEQ ID NO: 14) | GGCGCCCGGTATTTGTTAAAAGCGG<u>CACCCGCATCATGTAGA</u>TAGTCAAGACGAGCAGTCCGAAGCGATCGC (SEQ ID NO: 35) |
| 15 | CTCGTACGCGTG GAAA (SEQ ID NO: 15) | GGCGCCCGGTATTTGTTAAAAGCGG<u>CTCGTACGCGTGGAAA</u>TAGTCAAGACGAGCAGTCCGAAGCGATCGC (SEQ ID NO: 36) |
| 16 | TTAGTCAAAGAC GCCCGATT (SEQ ID NO: 16) | GGCGCCCGGTATTTGTTAAAAGCGG<u>TTAGTCAAAGACGCCCGATT</u>TAGTCAAGACGAGCAGTCCGAAGCGATCGC (SEQ ID NO: 37) |
| 17 | TATTCGCATCTG GGCGAT (SEQ ID NO: 17) | GGCGCCCGGTATTTGTTAAAAGCGG<u>TATTCGCATCTGGGCGAT</u>TAGTCAAGACGAGCAGTCCGAAGCGATCGC (SEQ ID NO: 38) |
| 18 | TCCTGAACTTCT ACATAGCT (SEQ ID NO: 18) | GGCGCCCGGTATTTGTTAAAAGCGG<u>TCCTGAACTTCTACATAGCT</u>TAGTCAAGACGAGCAGTCCGAAGCGATCGC (SEQ ID NO: 39) |
| 19 | ACTGCCAGTTAG CTGC (SEQ ID NO: 19) | GGCGCCCGGTATTTGTTAAAAGCGG<u>ACTGCCAGTTAGCTGC</u>TAGTCAAGACGAGCAGTCCGAAGCGATCGC (SEQ ID NO: 40) |

TABLE 1-continued

Sequences of UGEs and of amplicons comprising a specific
UGE (underlined) and universal primer binding sites

| UGE No. | UGE Sequence | Amplicon Sequence |
|---|---|---|
| 20 | TCAGTCGCAACT AGCGAA (SEQ ID NO: 20) | GGCGCCCGGTATTTGTTAAAAGCGG<u>TCAGTCGCAACTAGC GAA</u>TAGTCAAGACGAGCAGTCCGAAGCGATCGC (SEQ ID NO: 41) |
| 21 | CGATAGCTTTCG AAGTACT (SEQ ID NO: 21) | GGCGCCCGGTATTTGTTAAAAGCGG<u>CGATAGCTTTCGAAG TACT</u>TAGTCAAGACGAGCAGTCCGAAGCGATCGC (SEQ ID NO: 42) |

Sets of modified high copy plant transformation vectors were constructed by cloning a selected amplicon fragment comprising a UGE, unique to the set, into NarIII and AsiSI sites of a progenitor plant transformation vector (an *Agrobacterium* binary vector). The amplicon fragments were commonly positioned between the promoter region of a gene designed to serve as a plant selectable marker (e.g., a herbicide tolerance gene) and the (oppositely-oriented) promoter region of a first gene of interest. Often, other genes of interest were also included between the T-DNA borders.

Example 2: Maize Genomic DNA Extraction

Genomic DNA from single maize seed samples was extracted using a modified FastID™ method (FastID™ Genomic DNA 96-well Extraction Kit; GENETIC ID, Fairfield, Iowa). Seed samples were ground using ⅜ inch stainless steel balls in 4 mL polycarbonate vials (OPS Diagnostics LLC, Lebanon, N.J.) on a GENO/GRINDER™ 2010 (SPEX SAMPLEPREP, Metuchen, N.J.) for 2 minutes at 1500 rpm. 1 mL lysis buffer containing Proteinase K (FastID™ Genomic DNA Kit) was added to the single seed ground powder, and the slurry was further homogenized for 20 seconds at 1500 rpm. Vials were centrifuged for 3 minutes at 1450×g and 200 µL supernatant was transferred to KINGFISHER™ 96 well Deep Well plates (Thermo Fisher Scientific Inc., Indianapolis, Ind.) containing binding buffer with magnetic beads (MAGATTRACT™ Suspension G; Qiagen).

Alternatively, in experiments wherein the bulk ground powder was destined for Adventitious Presence testing, 600 µL lysis buffer was added, and the slurry was homogenized for 5 minutes at 1360 rpm on the GENO/GRINDER™ 2010. The samples were spun down for 5 minutes at 6800×g, and 200 µL supernatant was transferred to KINGFISHER™ plates containing the binding buffer with magnetic beads.

In both instances (single seed and bulk ground seed), DNA bound to the magnetic beads was washed and eluted using a KINGFISHER™ automatic DNA extraction platform. DNA was eluted in 200 µL 1×TE buffer (10 mM Tris HCL, 1 mM EDTA, pH 8.0), and was stored at 4° C. until further use. Extracted DNA was quantified using a QUANT-IT™ PICO GREEN DNA assay kit (MOLECULAR PROBES; Invitrogen, Carlsbad, Calif.), and buffer was added to a final concentration of 10 ng/µL.

Example 3: Production of Transgenic Maize Plants

Immature embryos were isolated from ears of *Zea mays* inbred line B104 when the embryos were about 1.8 to 2.4 mm in length. The embryos were incubated with an *Agrobacterium* suspension containing acetosyringone and the surfactant, BREAK THRU™ S-233 at an Optical Density of 1.0 for 20 to 30 minutes, and then placed on co-cultivation medium, oriented scutellum-up.

The co-cultivation step was continued for 3 to 4 days, then the embryos were transferred onto plant tissue culture medium containing antibiotics for 7 days to suppress *Agrobacterium* growth and initiate callus formation. Calli were moved to medium containing an appropriate selection agent to suppress growth of non-transformed tissue for 3 weeks, and then were placed on selection medium containing plant growth hormones for 7 days to induce somatic embryo germination. After one week of exposure to the plant growth hormone medium, calli were placed on a plant regeneration medium with selection.

Plants typically formed within 1 to 2 weeks after being transferred to the plant regeneration medium, and as plantlets developed, they were moved to plant growth medium. 10-15 mg leaf tissue from each plant were sampled for hydrolysis probe PCR analysis of the selectable marker gene (AAD1; U.S. Pat. No. 7,838,733) one week before 30 to 40 low-copy-number events (i.e., 1 to 3 copies of the selectable marker gene) per construct were transferred to the greenhouse for transplantation and growth in greenhouse. All $T_0$ events were de-tasseled and pollinated with B104 pollen for $T_1$ seed production. $T_1$ and $T_2$ plants were self-pollinated to produce homozygous seeds.

Example 4: Detection of Unique Genetic Elements Comprised in a Vector Set

Individual UGEs in plasmid DNA containing the UGE amplicons were detected using a PCR method with a unique hydrolysis oligonucleotide probe. Universal primers were used in the PCR assays for amplification and detection of UGEs from different groups of constructs. Universal primers used to amplify the amplicons listed in Table 1 are described in Table 2. Quenchable fluorescence-based PCR hydrolysis probes were designed to be specifically hybridizable to target UGEs, and were labeled with FAM fluorescence reporter dye (MGBNFQ as quencher). Hydrolysis probe oligonucleotides comprised a nucleotide sequence identical to the UGE to be detected.

Pre-validation of UGEs was carried out by testing serial dilutions of UGE-containing plasmid DNA by themselves, and non-transgenic corn genomic DNA spiked with varying concentrations of UGE-containing plasmid DNA. Thus, primers and hydrolysis probes were also designed to amplify and specifically hybridize to target corn internal controls, ZSSIIb (SEQ ID NO:48) and Invertase (SEQ ID NO:47). Table 3. These control probes were labeled with HEX fluorescence reporter dye (BHQ2 as quencher). Primers and probes were obtained from Applied BioSystems (Carlsbad, Calif.) or Integrated DNA Technologies (Coralville, Iowa). PCR reagents were obtained from Qiagen (Valencia, Calif.).

TABLE 2

Primer pairs and sequences of PCR primers used to amplify fragments comprising UGEs for hydrolysis probe assays.

| Alternative Universal Primer Sets | Primer Sequence | Used to Detect UGE Nos. |
|---|---|---|
| Forward Primer | TGCAGGTCAATCCCATTGC (SEQ ID NO: 43) | 1-6 |
| Reverse Primer | CAAGCATATGAATGACCTCGAGAA (SEQ ID NO: 44) | |
| Forward Primer | CGCCCGGTATTTGTTAAAAGC (SEQ ID NO: 45) | 7-21 |
| Reverse Primer | CTTCGGACTGCTCGTCTTGAC (SEQ ID NO: 46) | |

TABLE 3

PCR primer and probe sequences used to detect maize internal control genes.

| Invertase | | |
|---|---|---|
| Forward Primer | TGGCGGACGACGACTTGT (SEQ ID NO: 49) | |
| Reverse Primer | AAAGTTTGGAGGCTGCCGT (SEQ ID NO: 50) | |
| Probe Oligonucleotide | CGAGCAGACCGCCGTGTACTTCTACC (SEQ ID NO: 51) | |
| ZSSIIb | | |
| Forward Primer | CTCCCAATCCTTTGACATCTGC (SEQ ID NO: 52) | |
| Reverse Primer | TCGATTTCTCTCTTGGTGACAGG (SEQ ID NO: 53) | |
| Probe Oligonucleotide | AGCAAAGTCAGAGCGCTGCAATGCA (SEQ ID NO: 54) | |

Validation by Hydrolysis Probe PCR assays demonstrated that individual UGEs were detected with high accuracy, specificity, and efficiency. End-point and real-time PCR techniques were utilized to detect UGEs from plasmids and corn genomic DNA, according to the conditions in Tables 4-5. Biplex PCR assays (TAQMAN®) were performed to detect both the target (UGE) as well as the internal control (Invertase or ZSSIIb).

TABLE 4

Components of the PCR reaction.

| Component | Stock Concentration | Reagent Volume (μL) | Final Concentration |
|---|---|---|---|
| PCR Buffer (with 10 mM MgCl$_2$) | 10x | 1.5 | 1.25x |
| MgCl$_2$ | 25 mM | 1.5 | 3.125 mM |
| dNTP mix (10 mM; 2.5 mM each dNTP) | 10 mM | 1.2 | 1 mM |
| UGE Target-Forward Primer | 20 μM | 0.3 | 0.5 μM |
| UGE Target-Reverse Primer | 20 μM | 0.3 | 0.5 μM |
| UGE Target-FAM-Probe | 10 μM | 0.06 | 0.05 μM |
| Internal Control-Forward Primer* | 20 μM | 0.1 | 0.167 μM |
| Internal Control-Reverse Primer* | 20 μM | 0.1 | 0.167 μM |
| Internal Control-HEX-Probe* | 10 μM | 0.06 | 0.05 μM |
| HOTSTART ™ Taq Polymerase | 5 U/μL | 0.1 | 0.042 U/μL |
| Water** | | 6.78 | |
| Total Volume | | 12 μL | |

*As appropriate; included in experiments containing maize genomic DNA.
**As appropriate to adjust total volume to 12 μL After PCR mixes were made (Table 4), 7 μL of mix (for a 384-well plate) or 12 μL of mix (for a 96-well plate) were transferred into each well, and 3 μL of DNA sample (up to 30 ng/reaction) were added. The PCR plates were sealed with a FLEXISEAL™ membrane, and the reactions were run in a thermocycler.

Different PCR conditions were utilized to detect UGEs in plasmid samples (Table 5a), when the UGE plasmids were spiked into genomic DNA prepared from non-transgenic maize (Table 5b), or when UGEs were assayed in genomic DNA prepared from transgenic maize (Table 5c). In experiments wherein the UGE plasmids were spiked into maize genomic DNA, and when UGEs were assayed in transgenic maize DNA, biplex hydrolysis probe PCR assays were carried out to detect both the UGE and the maize internal control (reference) genes (invertase or ZSSIIb). For end-point PCR reactions, either a C1000 thermocycler (BIO-RAD) or a PE9700 thermocycler (PERKIN ELMER) was used. For real-time PCR reactions, a LIGHTCYCLER® II thermocycler (ROCHE) was used.

TABLE 5

PCR Reaction Parameters.

| Step | Temp. (° C.) | Time | No. Cycles |
|---|---|---|---|
| 5a. End-point hydrolysis probe PCR program for detection of UGEs in plasmid DNAs | | | |
| Activation | 95 | 15 min | 1 |
| Denaturation | 95 | 30 sec | 40 |
| Annealing | 52 | 30 sec | |
| Extension | 72 | 30 sec | |
| Terminal Extension | 72 | 5 min | 1 |
| Cooling | 4 | Hold | 1 |
| 5b. Real-time hydrolysis probe PCR program for detection of UGEs in plasmids spiked into non-transgenic maize genomic DNA | | | |
| Activation | 95 | 15 min | 1 |
| Denaturation | 95 | 30 sec | 50 |
| Annealing | 52 | 30 sec | |
| Extension | 72 | 30 sec | |
| Terminal Extension | 72 | 5 min | 1 |
| Cooling | 4 | Hold | 1 |
| 5c. End-point hydrolysis probe PCR program for detection of UGEs in transgenic maize genomic DNA | | | |
| Activation | 95 | 15 min | 1 |
| Denaturation | 95 | 30 sec | 40 |
| Annealing | 60 | 30 sec | |
| Extension | 72 | 30 sec | |
| Terminal Extension | 72 | 5 min | 1 |
| Cooling | 4 | Hold | 1 |

Completed PCR plates were read on a PHERASTAR™ FS fluorescence plate reader (BMG LABTECH; Cary, N.C.).

Figure 1:
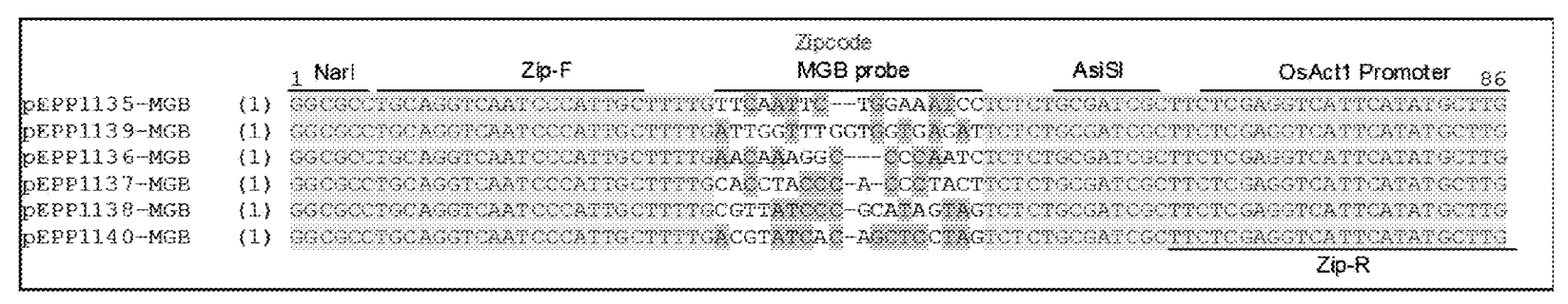

Amplicons comprising one of six UGEs (Table 1; UGE1-UGE6) were synthesized and cloned into high copy number plasmids, and appropriate plasmid DNAs (i.e. pEPP1135 to pEPP1140; corresponding to UGE1-UGE6, respectively) were used for testing PCR amplification and detection efficiency, specificity, and sensitivity in the end-point PCR reactions. Sequences of polynucleotides comprising the six UGEs and flanking elements were aligned in Vector NTI to show the differences in nucleotide sequence. FIG. 1.

Specificity of UGE Detection

Hydrolysis probes (labeled with FAM fluorescent dye) targeting the six UGEs were tested against each of the UGE plasmid DNAs (pEPP1135-pEPP1140). Each designed hydrolysis probe targeting one of the six different UGEs specifically amplified the target UGE (marked with circles), and no non-specific amplification/cross-reactivity was seen from other probes. FIG. 2. The hydrolysis probes were shown to distinguish between all six different UGE-containing cassettes in plasmid DNA (pEPP1135-pEPP1140). Probes were also tested against no template control and negative control corn DNA to rule out any non-specific binding. FIG. 2.

Sensitivity of UGE Detection

Figure 3:
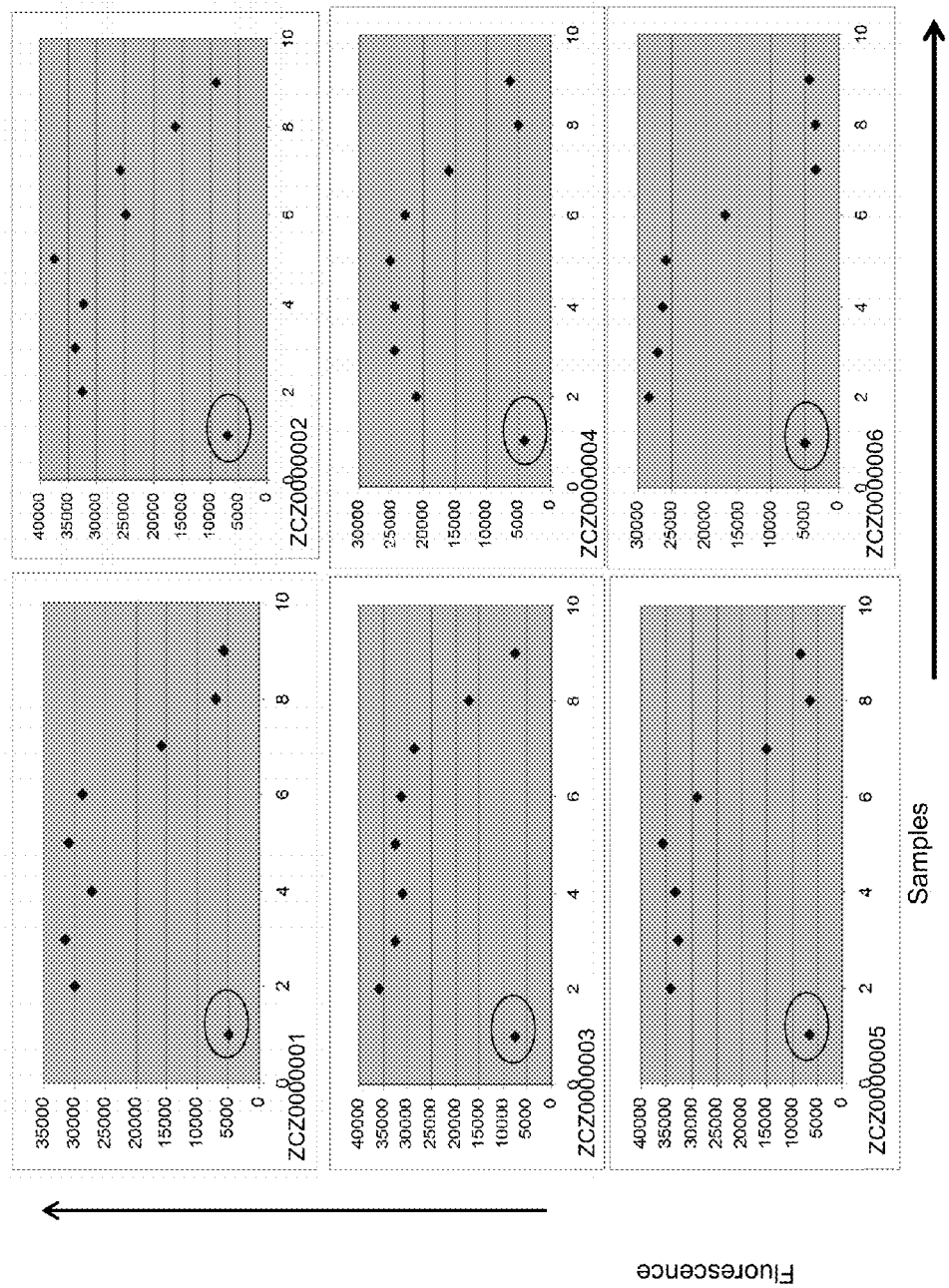
FIG. 3 includes detection results showing that extremely low concentrations of target UGE DNA can be detected using hydrolysis probes designed to specifically hybridize thereto. Template (plasmid DNA) concentrations ranging from 0.0000001 ng to 1 ng were tested (shown from left to right orientation) in end-point PCRs. No-template control was included to test the non-specificity (marked in circle).

Using appropriate UGE template/hydrolysis probe combinations for each of the UGE-containing plasmids, hydrolysis probe assay end-point PCR reactions were performed to determine the level of method sensitivity. Plasmid DNA containing the UGEs was used as template for PCR amplification. Concentrations ranging from 0.0000001 ng to 1 ng plasmid DNA were tested. Results showed that very low concentrations of UGE-containing template DNA can be detected with all the hydrolysis probes. FIG. 3. Probes were also tested against no template control and negative control corn DNA to rule out any non-specific binding. FIG. 3.

Figure 4:
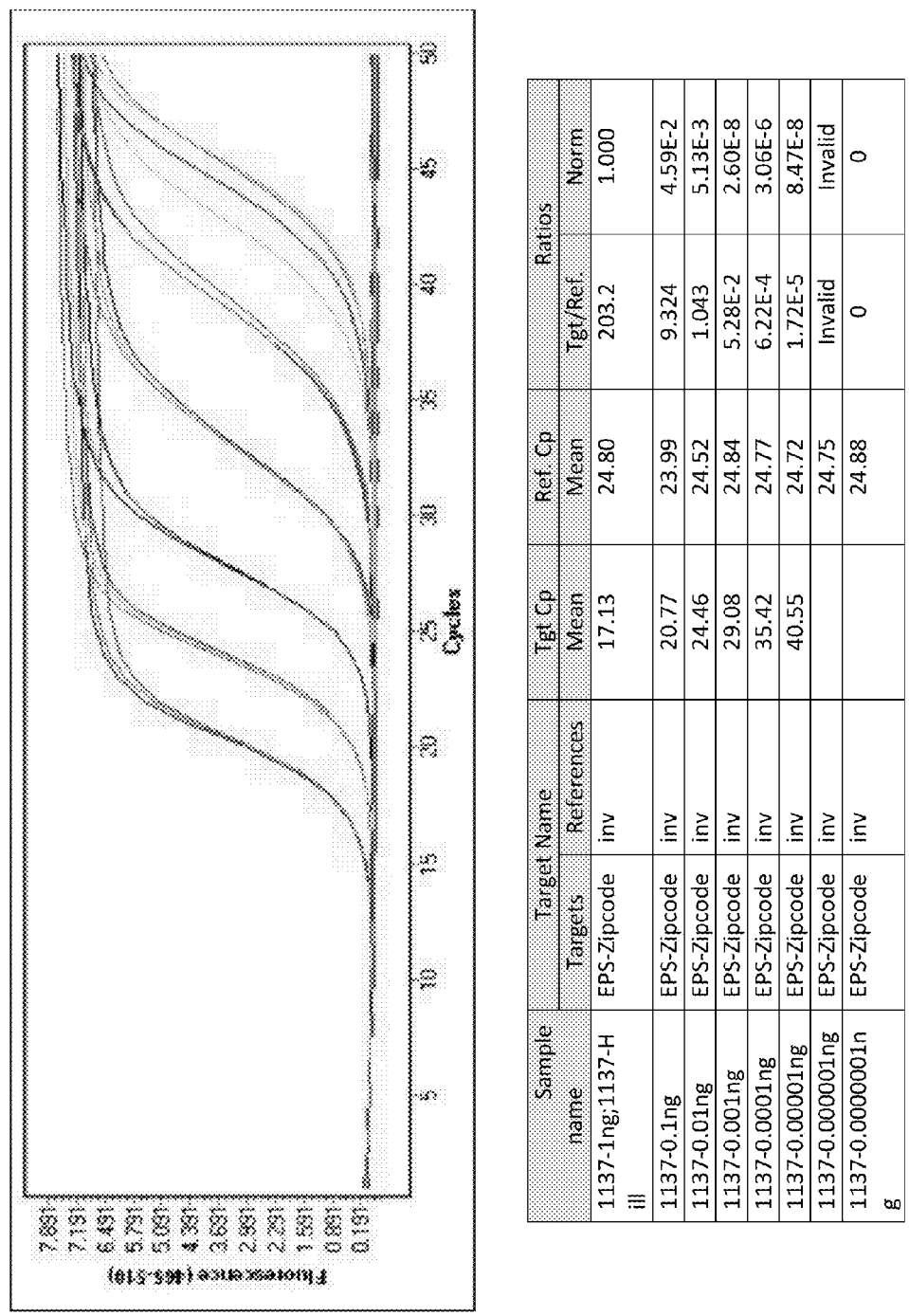
FIG. 4 includes detection results of a plasmid comprising a target UGE (SEQ ID NO:3) in a non-transgenic corn genomic DNA background using a fluorescence-based hydrolysis PCR assay. Melting curve analysis and cycle number for target and internal control crossing points (Cp) are presented.
Figure 5:
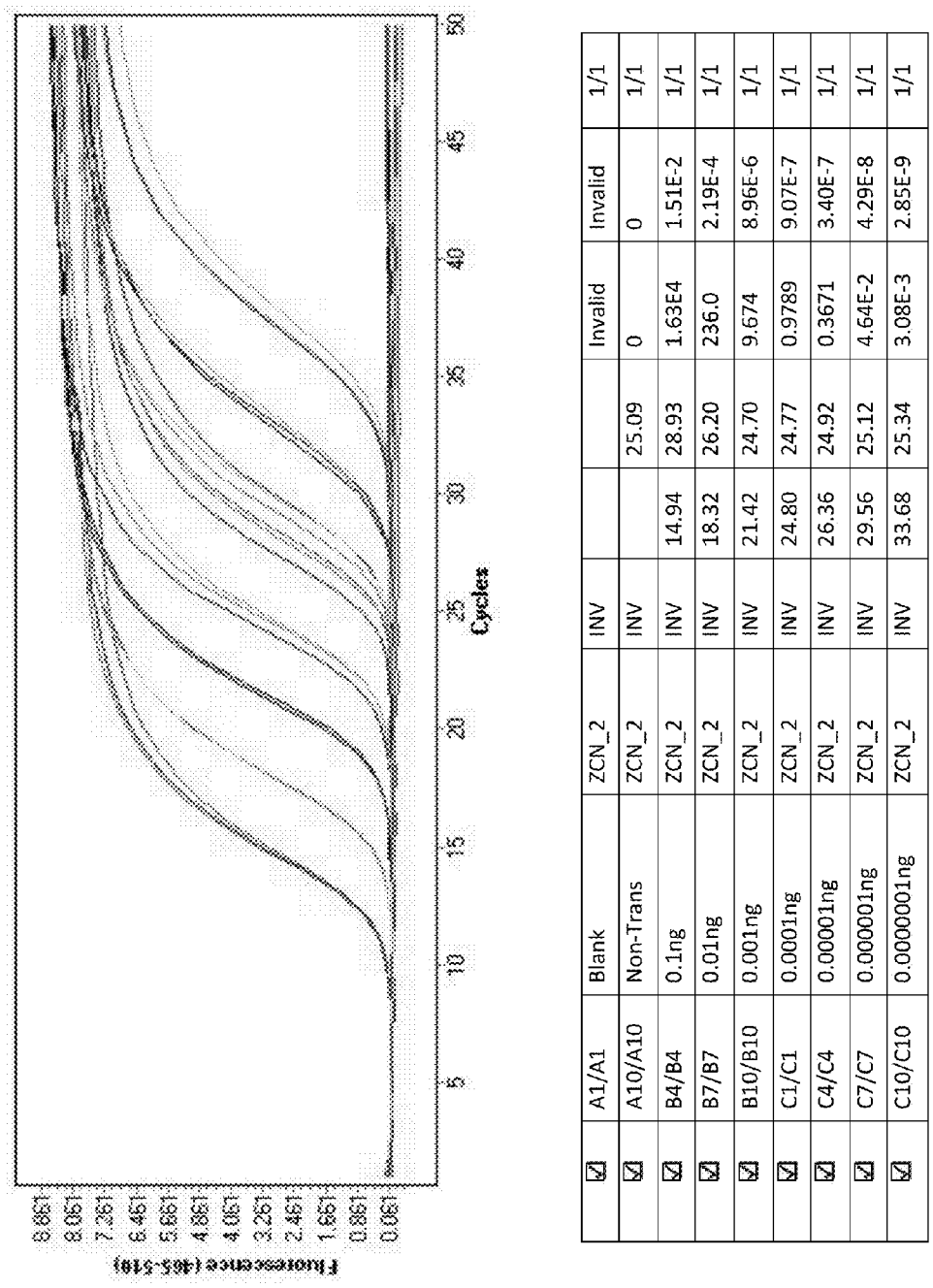
FIG. 5 includes detection results of a plasmid comprising a target UGE (SEQ ID NO:8) in a non-transgenic corn genomic DNA background using a fluorescence-based hydrolysis PCR assay. Melting curve analysis and cycle number for target and internal control crossing points (Cp) are presented.

Example 5: Specific and Sensitive Detection of Unique Genetic Elements in Maize DNA Detection of UGE DNA in Non-Transgenic Maize Genomic DNA UGEs (UGE2, UGE3, and UGE7-UGE21) were detected by real-time hydrolysis probe PCR when spiked into a background of maize genomic DNA. Dilutions ranging from 0.0000001 ng to 1 ng were tested. Real-time PCRs were performed using the LIGHTCYCLER™ II thermocycler. Melting curves were analyzed and mean Cp values were calculated for each target DNA dilution. Detection limits determined for each of the UGEs tested are listed in Table 6. Examples of individual assays (detection of UGE3 and UGE4) are shown in FIG. 4 and FIG. 5, respectively. These PCR results demonstrated the feasibility of detecting UGEs with high sensitivity, which suggests that UGEs can provide a novel tool to detect plant transformation constructs.

TABLE 6

Limits of detection for UGEs when spiked into non-transgenic maize genomic DNA. "Lowest Amount Detected" represents the limit of detection for each UGE in a hydrolysis probe real-time PCR assay.

| UGE No. | Lowest Amount Detected (ng) |
| --- | --- |
| 2 | 0.0001 |
| 3 | 0.00001 |
| 7 | 0.0000001 |

TABLE 6-continued

Limits of detection for UGEs when spiked into non-transgenic maize genomic DNA. "Lowest Amount Detected" represents the limit of detection for each UGE in a hydrolysis probe real-time PCR assay.

| UGE No. | Lowest Amount Detected (ng) |
| --- | --- |
| 8 | 0.0000001 |
| 9 | 0.0000001 |
| 10 | 0.0000001 |
| 11 | 0.000001 |
| 12 | 0.0000001 |
| 13 | 0.0000001 |
| 14 | 0.000001 |
| 15 | 0.0000001 |
| 16 | 0.000001 |
| 17 | 0.000001 |
| 18 | 0.0000001 |
| 19 | 0.000001 |
| 20 | 0.0000001 |
| 21 | 0.000001 |

Detection of UGEs in Genomic DNA from Seeds of Transgenic Maize Plants.

Figure 6:
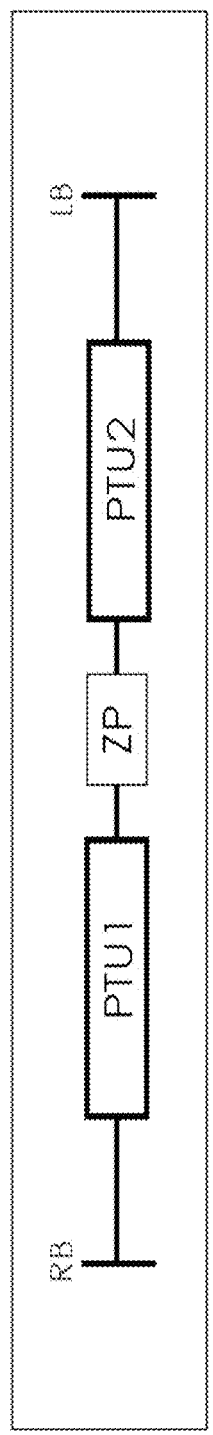
FIG. 6 includes a schematic showing a UGE cloning strategy. In the schematic, "PTU" represents a Plant Transformation Unit and "ZP" represents the amplicon comprising the UGE. "LB" and "RB" represent Left and Right borders of T-DNA, respectively.
Figure 7:
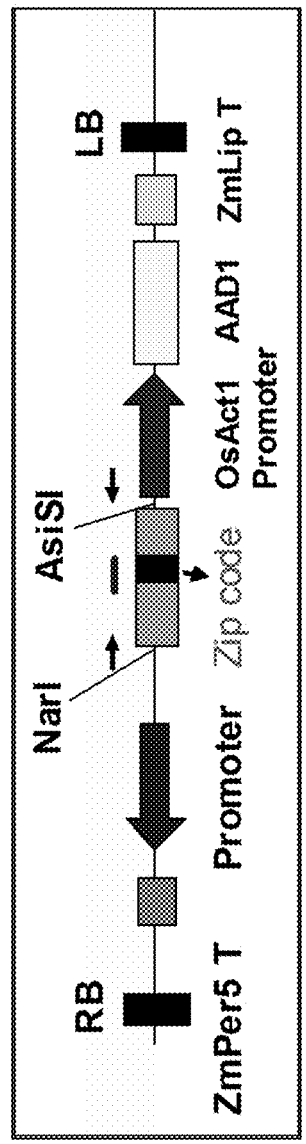
FIG. 7 includes a schematic showing an example of a UGE cloning strategy for agronomic trait projects. This example illustrates that a UGE was cloned between a selectable marker (OsAct1-AAD1-ZmLip) and the agronomic gene of interest.

UGE amplicons were further cloned into plant transformation vectors following the strategy described in FIGS. 6-7. Twelve amplicons comprising a UGE were used in 366 plant expression vectors carrying different genes of interest, and nearly 8,000 transgenic events were generated. Table 7.

TABLE 7

Amplicons comprising a UGE incorporated into plant transformation vectors.

| UGE No. | Number of Constructs | Number of $T_1$ Events with Seeds |
| --- | --- | --- |
| 1 | 25 | 1127 |
| 2 | 26 | 594 |
| 3 | 20 | 711 |
| 4 | 23 | 1048 |
| 5 | 25 | 997 |
| 6 | 24 | 939 |
| 7 | 72 | 538 |
| 8 | 25 | 922 |
| 9 | 25 | 800 |
| 10 | 27 | 150 |
| 11 | 61 | |
| 12 | 13 | |
| Total | 366 | 7826 |

Genomic DNA isolated from seeds of heterozygous $T_1$ transgenic events obtained by transformation with constructs that contained UGE2 and UGE3 were used for testing UGE detection (seed sources are listed in Table 8). Genomic DNA was isolated as described earlier. The concentration of the genomic DNA was adjusted to 10 ng/μL, and a total of 30 ng genomic DNA was used for each PCR reaction. Non-transgenic corn seed DNA was used as a negative control.

TABLE 8

Materials used for UGE detections in genomic DNA prepared from seeds of heterozygous transgenic maize plants.

| UGE No. | Seed ID | Event ID | Transforming Plasmid |
| --- | --- | --- | --- |
| 2 | ZT00274311 | ZX17897-0859190 | pDAB106476 |
| 2 | ZT00276232 | ZX18037-0867761 | pDAB106479 |
| 2 | ZT00328210 | ZX18758-0889569 | pDAB106529 |
| 3 | ZT00305360 | ZX20077-0912363 | pDAB108323 |

TABLE 8-continued

Materials used for UGE detections in genomic DNA prepared from seeds of heterozygous transgenic maize plants.

| UGE No. | Seed ID | Event ID | Transforming Plasmid |
|---|---|---|---|
| 4 | ZT00328418 | ZX19537-0906115 | pDAB108526 |
| 4 | ZT00297283 | ZX19538-0905769 | pDAB108527 |

Figure 8:
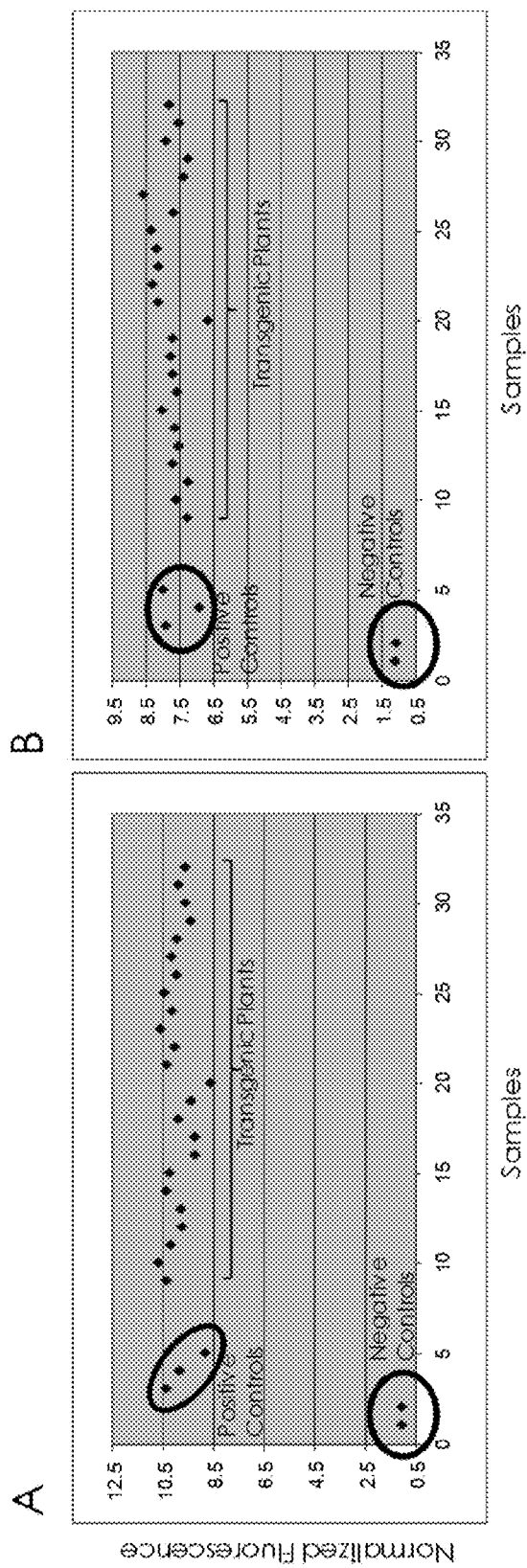
FIG. 8 includes data showing detection of UGE sequences in $T_1$ transgenic corn seed. Positive controls: Plasmid DNA containing the UGE sequences; Negative controls: Non-transgenic corn genomic DNA; 8A: Transgenic corn seed containing UGE2; 8B: Transgenic corn seed containing UGE3.

UGE-specific end-point hydrolysis probe PCR assays were run, and the results were analyzed as a function of normalized fluorescence vs. sample number. FIG. 8. The results showed a sensitive amplification and detection of target UGE sequences from transgenic samples and no amplification from non-transgenic corn samples, thereby demonstrating the specificity of the detection method.

Example 6: Use of Unique Genetic Elements for Adventitious Presence Testing

To test the use of UGEs for adventitious presence detection, $T_2$ homozygous seeds were obtained from transgenic plants produced by transformation with constructs containing UGE3 (seed sources listed in Table 9). In total, 35 homozygous transgenic seeds per event were chosen and genomic DNA was isolated.

TABLE 9

Identities of materials used for UGE3 detection in genomic DNA prepared from seeds of homozygous $T_2$ transgenic maize plants.

| Pedigree | Source ID |
|---|---|
| B104/ pDAB108526{ZX19537}0906118.001-B | ZQ11LQ199088.0016.016 |
| B104/ pDAB108526{ZX19537}0906133.001-B | ZQ11LQ199111.0092.092 |
| B104/ pDAB108527{ZX19538}0907077.001-B | ZQ11LQ199735.2436.2436 |
| B104/ pDAB108527{ZX19698}0907681.001-B | ZQ11LQ199785.2620.2620 |
| B104/ pDAB108528{ZX19737}0908226.001-B | ZQ11LQ199807.2688.2688 |
| B104/ pDAB108528{ZX19737}0908230.001-B | ZQ11LQ199831.2740.2740 |

Figure 9:
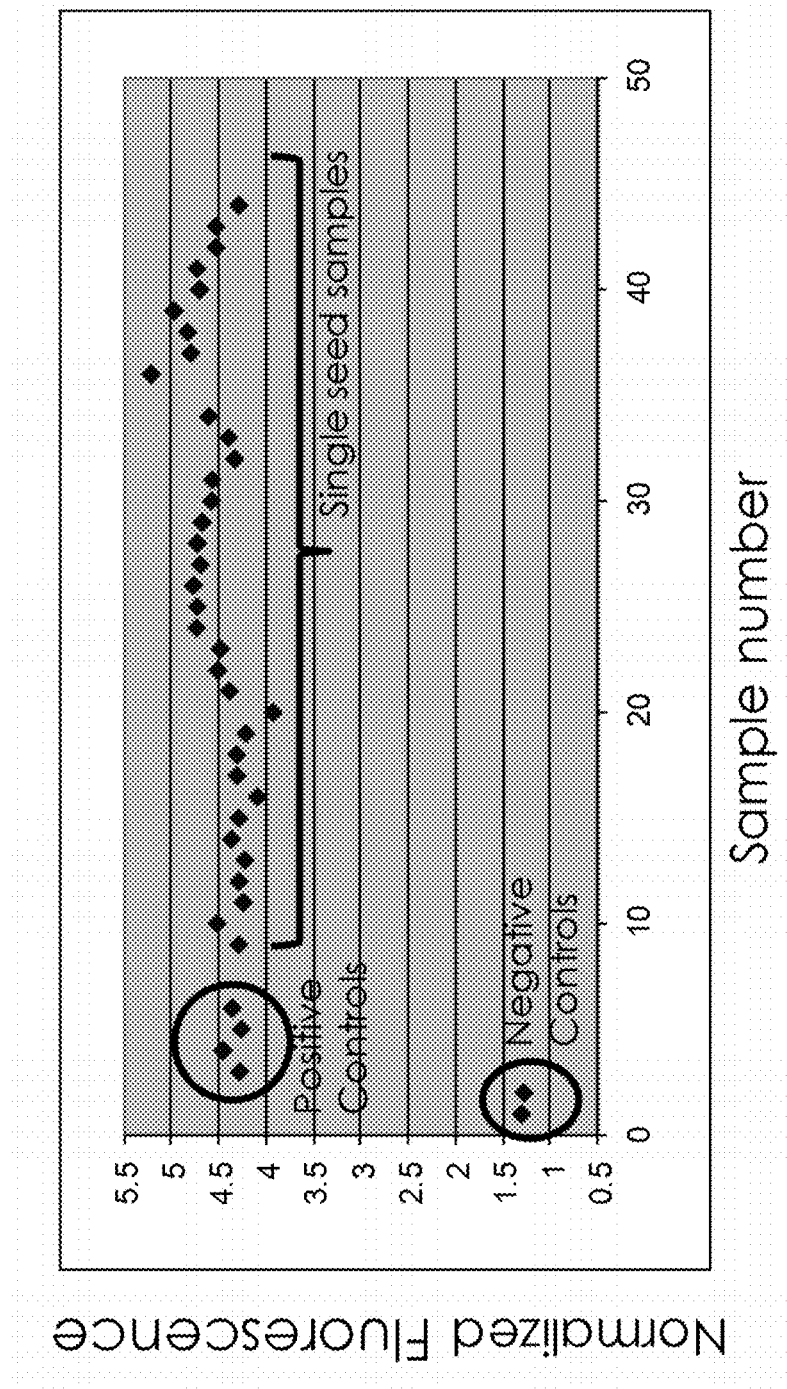
FIG. 9 includes data showing detection of a UGE sequence (UGE3) in homozygous transgenic corn seed samples. Negative controls—Non-transgenic corn DNA; Positive controls—ZCZ0000003 plasmid DNA; Samples—Transgenic $T_2$ corn seed DNA expressing UGE3 (pDAB108526, pDAB108527, pDAB108528; 6 different seed sources were used as listed in Table 9).

UGE-specific end-point hydrolysis probe PCR assays were run, and the results were analyzed as described in Example 5. The results showed clear amplification of target UGE3 sequences from the homozygous transgenic samples and positive control samples, and no amplification from non-transgenic maize samples (negative controls). FIG. 9.

Samples of maize genomic DNA prepared from 35 homozygous seeds of transgenic Source ID No. ZQ11LQ199088.0016.016 (Table 9) were pooled and serial dilutions (100%, 10%, 1%, 0.5% and 0.1% transgenic DNA) were generated using non-transgenic maize genomic DNA as the background (diluent). Six replicates of each transgenic DNA dilution were run in end-point hydrolysis probe PCR assays (40 cycles).

Figure 10:
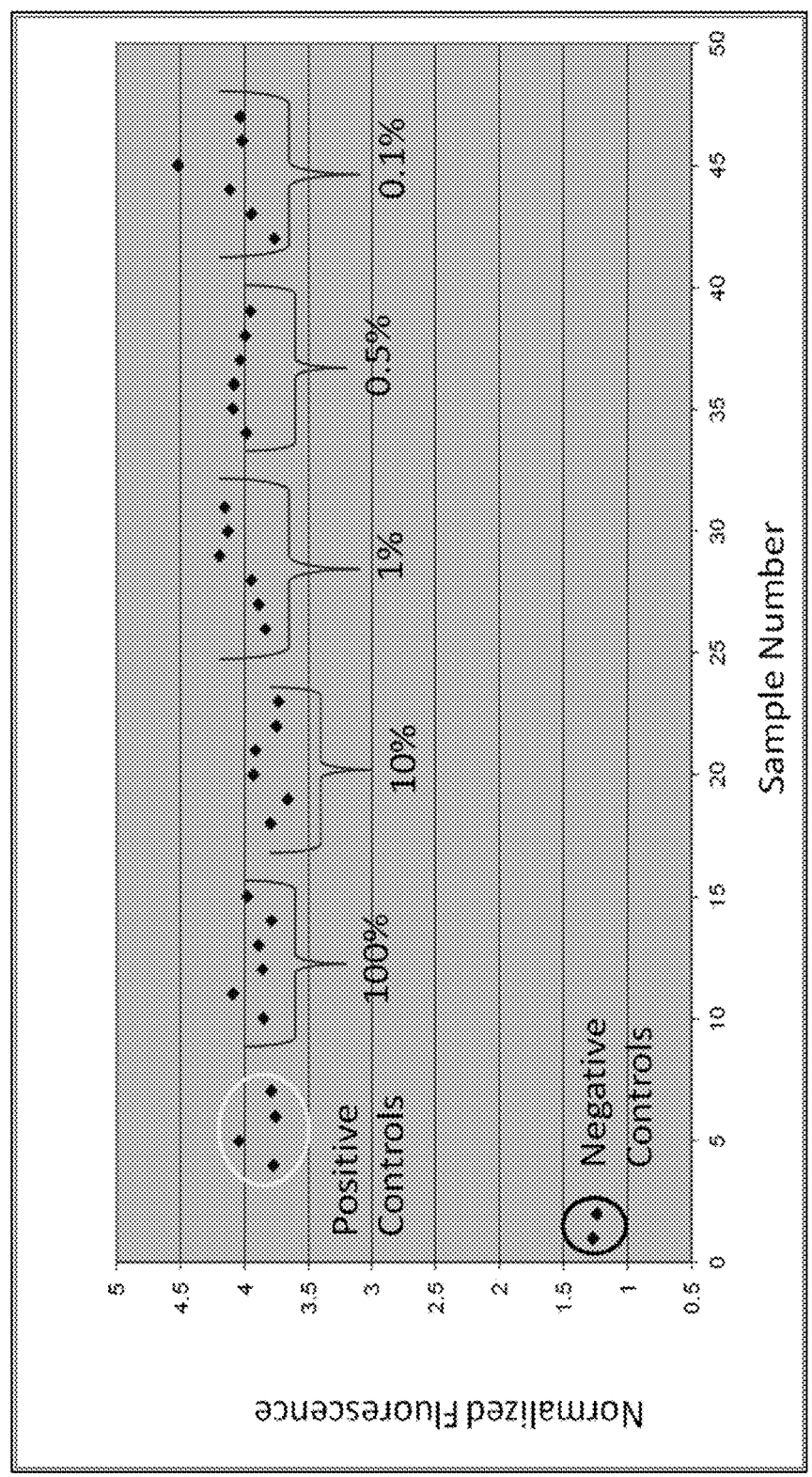
FIG. 10 includes data showing the sensitivity of UGE detection from transgenic maize (UGE3). Negative controls—Non-transgenic corn DNA; Positive controls—ZCZ0000003 plasmid DNA Samples—Dilutions of transgenic $T_2$ corn seed DNA (pDAB108526—Source ID # ZQ11LQ199088.0016.016).

Results were analyzed as a function of relative fluorescence vs. sample number. FIG. 10. Measured relative fluorescence from all of the dilutions was detected. No non-specific amplification was observed from negative samples (no template control and non-transgenic DNA controls). These results demonstrate that UGEs can be detected in genomic DNA prepared from transgenic maize seeds with extremely high sensitivity and accuracy.

Figure 11:
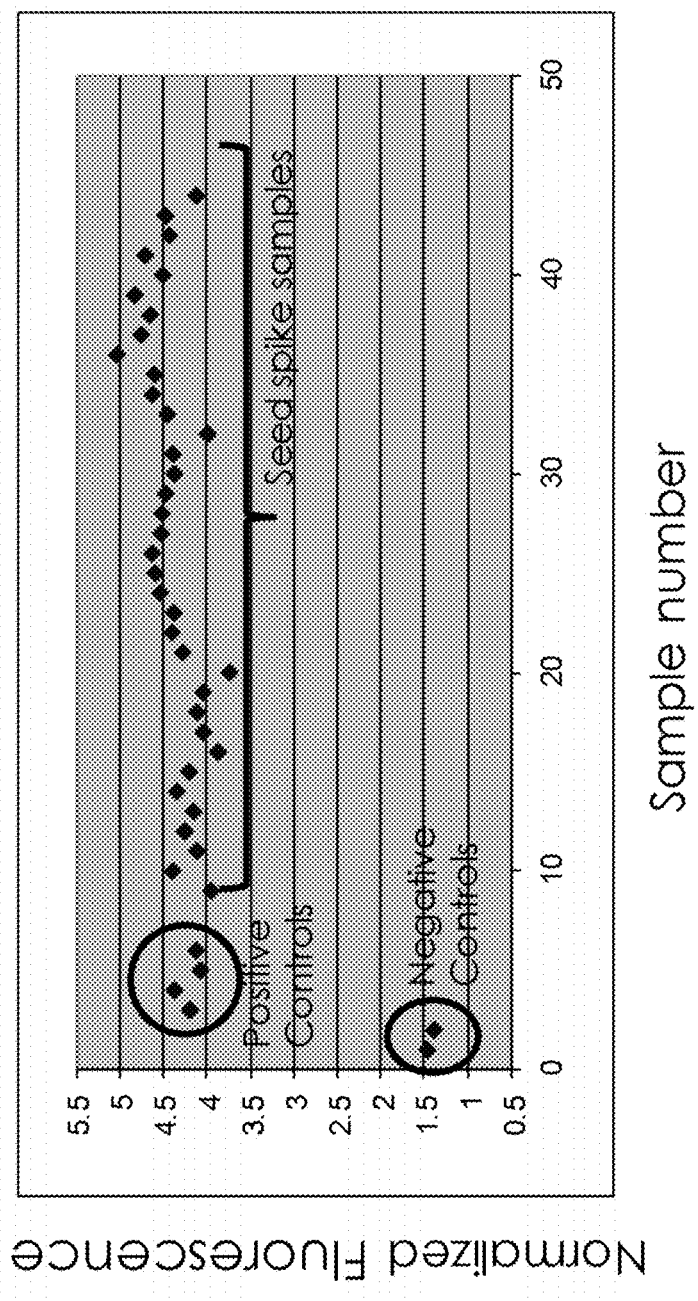
FIG. 11 includes data demonstrating the detection of a UGE in a spiked transgenic seed sample with a hydrolysis probe PCR Assay. Negative controls—Non-transgenic corn DNA; Positive controls—1% genomic DNA; Samples—36 DNA samples from spiked corn seed (1 transgenic seed in 99 non-transgenic seed)—12 biological replicates and 3 technical replicates.

Pools of 100 seed are typically tested for adventitious presence, which requires a suitable detection method to identify a single contaminating transgenic seed among 99 non-transgenic seeds, which equals a 1% sensitivity requirement. A single transgenic $T_2$ corn seed (pDAB108526—Source ID # ZQ11LQ199088.0016.016) containing a UGE (UGE3) was spiked into a pool of 99 non-transgenic corn seeds. Isolated DNA from the seed pool was tested using the end-point hydrolysis probe PCR. Results demonstrated that contaminating seed can be easily detected using the UGE-specific assay (FIG. 11), further strengthening the argument that UGEs can be used for AP testing, and for monitoring transgenic events.

What is claimed is:

1. A method for identifying in a sample comprising plant DNA, a plurality of heterologous polynucleotides, wherein each of the heterologous polynucleotides comprises, in the 5' to 3' direction, a first nucleotide sequence that is identical between all of the members of the plurality of heterologous polynucleotides; a second nucleotide sequence that is unique among all of the members of the plurality of heterologous polynucleotides; and a third nucleotide sequence that is identical between all of the members of the plurality of heterologous polynucleotides, the method comprising:
contacting the plant DNA in the sample with:
a first oligonucleotide primer that specifically hybridizes to the first nucleotide sequence, and
a second oligonucleotide primer that specifically hybridizes to the third nucleotide sequence;
amplifying in a polymerase chain reaction (PCR) a plurality of amplicons, each containing the second nucleotide sequence that is present in a member of the plurality of heterologous polynucleotides; and
contacting the amplicons with a detectable probe molecule that specifically hybridizes to a binding site in the second nucleotide sequence in a member of the plurality of heterologous polynucleotides, wherein the binding site is selected from the group consisting of SEQ ID NO 1-21 and the complements thereof.

2. The method according to claim 1, wherein each of the members of the plurality of heterologous polynucleotides comprises a gene in the second nucleotide sequence, and wherein the binding site for the detectable probe molecule is located outside the gene in the second nucleotide sequence of each of the members of the plurality of heterologous polynucleotides.

3. The method according to claim 1, wherein the detectable probe molecule comprises a fluorophore and a quencher, and wherein specific hybridization of the probe to the binding site in the second nucleotide sequence releases the fluorophore from the quencher in the probe molecule, thereby producing a detectable fluorescence signal.

4. The method according to claim 1, wherein the amplicons amplified in the PCR reaction are each between about 70 and about 80 nucleotides in length.

5. The method according to claim 1, wherein the second nucleotide sequence of each of the members of the plurality of heterologous polynucleotides is between about 15 and about 25 nucleotides in length.

6. The method according to claim 1, wherein at least one of the heterologous polynucleotides consists of, in the 5' to 3' direction: the first nucleotide sequence, the second nucleotide sequence, and the third nucleotide sequence.

7. The method according to claim 1, wherein the steps of the method are performed in an end-point PCR reaction.

8. The method according to claim 1, wherein the steps of the method are performed in a real-time PCR reaction.

9. The method according to claim 1, wherein the plant DNA comprises the heterologous polynucleotides in a total amount of at least about $8.33 \times 10^8$% compared to the total amount of DNA in the sample, and a detectable signal is produced by the probe, indicating specific hybridization to the binding site in the second nucleotide sequence.

10. The method according to claim 1, wherein at least one of the plurality of heterologous polynucleotides comprises an agronomic gene of interest.

11. The method according to claim 1, wherein contacting the amplicons with the detectable probe molecule does not produce a detectable signal, indicating that the DNA sample does not comprise any of the heterologous polynucleotides.

12. The method according to claim 11, wherein the heterologous polynucleotides are selected from the group consisting of SEQ ID NOs:22-42 and the complements thereof.

* * * * *

SEQUENCE LISTING

```
<160> NUMBER OF SEQ ID NOS: 60

<210> SEQ ID NO 1
<211> LENGTH: 17
<212> TYPE: DNA
<213> ORGANISM: Artificial Sequence
<220> FEATURE:
<223> OTHER INFORMATION: Unique specifically detectable nucleotide
      sequence (UGE1)

<400> SEQUENCE: 1
ttcaattctg gaaatcc                                                   17

<210> SEQ ID NO 2
<211> LENGTH: 16
<212> TYPE: DNA
<213> ORGANISM: Artificial Sequence
<220> FEATURE:
<223> OTHER INFORMATION: Unique specifically detectable nucleotide
      sequence (UGE2)

<400> SEQUENCE: 2
```
aacaaaggcc ccaatc                                                          16

<210> SEQ ID NO 3
<211> LENGTH: 17
<212> TYPE: DNA
<213> ORGANISM: Artificial Sequence
<220> FEATURE:
<223> OTHER INFORMATION: Unique specifically detectable nucleotide
      sequence (UGE3)

<400> SEQUENCE: 3
cacctaccca ccctact                                                         17

<210> SEQ ID NO 4
<211> LENGTH: 18
<212> TYPE: DNA
<213> ORGANISM: Artificial Sequence
<220> FEATURE:
<223> OTHER INFORMATION: Unique specifically detectable nucleotide
      sequence (UGE4)

<400> SEQUENCE: 4
cgttatcccg catagtag                                                        18

<210> SEQ ID NO 5
<211> LENGTH: 19
<212> TYPE: DNA
<213> ORGANISM: Artificial Sequence
<220> FEATURE:
<223> OTHER INFORMATION: Unique specifically detectable nucleotide
      sequence (UGE5)

<400> SEQUENCE: 5
attggtttgg tggtgagat                                                       19

<210> SEQ ID NO 6
<211> LENGTH: 18
<212> TYPE: DNA
<213> ORGANISM: Artificial Sequence
<220> FEATURE:
<223> OTHER INFORMATION: Unique specifically detectable nucleotide
      sequence (UGE6)

<400> SEQUENCE: 6
acgtatcaca gctcctag                                                        18

<210> SEQ ID NO 7
<211> LENGTH: 19
<212> TYPE: DNA
<213> ORGANISM: Artificial Sequence
<220> FEATURE:
<223> OTHER INFORMATION: Unique specifically detectable nucleotide
      sequence (UGE7)

<400> SEQUENCE: 7
ttagtattgg cagcagacc                                                       19

<210> SEQ ID NO 8
<211> LENGTH: 20
<212> TYPE: DNA
<213> ORGANISM: Artificial Sequence
<220> FEATURE:
<223> OTHER INFORMATION: Unique specifically detectable nucleotide
      sequence (UGE8)

<400> SEQUENCE: 8
ccaataagac tgaagttgac                                                 20

<210> SEQ ID NO 9
<211> LENGTH: 18
<212> TYPE: DNA
<213> ORGANISM: Artificial Sequence
<220> FEATURE:
<223> OTHER INFORMATION: Unique specifically detectable nucleotide
      sequence (UGE9)

<400> SEQUENCE: 9
ctacctcgat cgcccata                                                   18

<210> SEQ ID NO 10
<211> LENGTH: 20
<212> TYPE: DNA
<213> ORGANISM: Artificial Sequence
<220> FEATURE:
<223> OTHER INFORMATION: Unique specifically detectable nucleotide
      sequence (UGE10)

<400> SEQUENCE: 10
tgttaggcta cgatagggtt                                                 20

<210> SEQ ID NO 11
<211> LENGTH: 16
<212> TYPE: DNA
<213> ORGANISM: Artificial Sequence
<220> FEATURE:
<223> OTHER INFORMATION: Unique specifically detectable nucleotide
      sequence (UGE11)

<400> SEQUENCE: 11
tacgcgcttc atccta                                                     16

<210> SEQ ID NO 12
<211> LENGTH: 19
<212> TYPE: DNA
<213> ORGANISM: Artificial Sequence
<220> FEATURE:
<223> OTHER INFORMATION: Unique specifically detectable nucleotide
      sequence (UGE12)

<400> SEQUENCE: 12
cgactcatca aacacgatt                                                  19

<210> SEQ ID NO 13
<211> LENGTH: 21
<212> TYPE: DNA
<213> ORGANISM: Artificial Sequence
<220> FEATURE:
<223> OTHER INFORMATION: Unique specifically detectable nucleotide
      sequence (UGE13)

<400> SEQUENCE: 13
acaattctca ctttcgtcta t                                               21

<210> SEQ ID NO 14
<211> LENGTH: 17
<212> TYPE: DNA
<213> ORGANISM: Artificial Sequence
<220> FEATURE:
<223> OTHER INFORMATION: Unique specifically detectable nucleotide
      sequence (UGE14)

<400> SEQUENCE: 14
cacccgcatc atgtaga                                                    17

<210> SEQ ID NO 15
<211> LENGTH: 16
<212> TYPE: DNA
<213> ORGANISM: Artificial Sequence
<220> FEATURE:
<223> OTHER INFORMATION: Unique specifically detectable nucleotide
      sequence (UGE15)

<400> SEQUENCE: 15
ctcgtacgcg tggaaa                                                    16

<210> SEQ ID NO 16
<211> LENGTH: 20
<212> TYPE: DNA
<213> ORGANISM: Artificial Sequence
<220> FEATURE:
<223> OTHER INFORMATION: Unique specifically detectable nucleotide
      sequence (UGE16)

<400> SEQUENCE: 16
ttagtcaaag acgcccgatt                                                20

<210> SEQ ID NO 17
<211> LENGTH: 18
<212> TYPE: DNA
<213> ORGANISM: Artificial Sequence
<220> FEATURE:
<223> OTHER INFORMATION: Unique specifically detectable nucleotide
      sequence (UGE17)

<400> SEQUENCE: 17
tattcgcatc tgggcgat                                                  18

<210> SEQ ID NO 18
<211> LENGTH: 20
<212> TYPE: DNA
<213> ORGANISM: Artificial Sequence
<220> FEATURE:
<223> OTHER INFORMATION: Unique specifically detectable nucleotide
      sequence (UGE18)

<400> SEQUENCE: 18
tcctgaactt ctacatagct                                                20

<210> SEQ ID NO 19
<211> LENGTH: 16
<212> TYPE: DNA
<213> ORGANISM: Artificial Sequence
<220> FEATURE:
<223> OTHER INFORMATION: Unique specifically detectable nucleotide
      sequence (UGE19)

<400> SEQUENCE: 19
actgccagtt agctgc                                                    16

<210> SEQ ID NO 20
<211> LENGTH: 18
<212> TYPE: DNA
<213> ORGANISM: Artificial Sequence
<220> FEATURE:
<223> OTHER INFORMATION: Unique specifically detectable nucleotide
      sequence (UGE20)

<400> SEQUENCE: 20
tcagtcgcaa ctagcgaa                                                  18

<210> SEQ ID NO 21
<211> LENGTH: 19
<212> TYPE: DNA
<213> ORGANISM: Artificial Sequence
<220> FEATURE:
<223> OTHER INFORMATION: Unique specifically detectable nucleotide
      sequence (UGE21)

<400> SEQUENCE: 21
cgatagcttt cgaagtact                                                   19

<210> SEQ ID NO 22
<211> LENGTH: 78
<212> TYPE: DNA
<213> ORGANISM: Artificial Sequence
<220> FEATURE:
<223> OTHER INFORMATION: Amplicon 1

<400> SEQUENCE: 22
tgcaggtcaa tcccattgct tttgttcaat tctggaaatc ctctctgcga tcgcttctcg      60
aggtcattca tatgcttg                                                   78

<210> SEQ ID NO 23
<211> LENGTH: 77
<212> TYPE: DNA
<213> ORGANISM: Artificial Sequence
<220> FEATURE:
<223> OTHER INFORMATION: Amplicon 2

<400> SEQUENCE: 23
tgcaggtcaa tcccattgct tttgaacaaa ggccccaatc tctctgcgat cgcttctcga      60
ggtcattcat atgcttg                                                    77

<210> SEQ ID NO 24
<211> LENGTH: 78
<212> TYPE: DNA
<213> ORGANISM: Artificial Sequence
<220> FEATURE:
<223> OTHER INFORMATION: Amplicon 3

<400> SEQUENCE: 24
tgcaggtcaa tcccattgct tttgcaccta cccaccctac ttctctgcga tcgcttctcg      60
aggtcattca tatgcttg                                                   78

<210> SEQ ID NO 25
<211> LENGTH: 79
<212> TYPE: DNA
<213> ORGANISM: Artificial Sequence
<220> FEATURE:
<223> OTHER INFORMATION: Amplicon 4

<400> SEQUENCE: 25
tgcaggtcaa tcccattgct tttgcgttat cccgcatagt agtctctgcg atcgcttctc      60
gaggtcattc atatgcttg                                                  79

<210> SEQ ID NO 26
<211> LENGTH: 80
<212> TYPE: DNA
<213> ORGANISM: Artificial Sequence
<220> FEATURE:
<223> OTHER INFORMATION: Amplicon 5

<400> SEQUENCE: 26

```
tgcaggtcaa tcccattgct tttgattggt tggtggtga gattctctgc gatcgcttct    60
cgaggtcatt catatgcttg                                                80
```

<210> SEQ ID NO 27
<211> LENGTH: 79
<212> TYPE: DNA
<213> ORGANISM: Artificial Sequence
<220> FEATURE:
<223> OTHER INFORMATION: Amplicon 6

<400> SEQUENCE: 27

```
tgcaggtcaa tcccattgct tttgacgtat cacagctcct agtctctgcg atcgcttctc    60
gaggtcattc atatgcttg                                                 79
```

<210> SEQ ID NO 28
<211> LENGTH: 78
<212> TYPE: DNA
<213> ORGANISM: Artificial Sequence
<220> FEATURE:
<223> OTHER INFORMATION: Amplicon 7

<400> SEQUENCE: 28

```
ggcgcccggt atttgttaaa agcggctact tagtattggc agcagaccta gtcaagacga    60
gcagtccgaa gcgatcgc                                                  78
```

<210> SEQ ID NO 29
<211> LENGTH: 75
<212> TYPE: DNA
<213> ORGANISM: Artificial Sequence
<220> FEATURE:
<223> OTHER INFORMATION: Amplicon 8

<400> SEQUENCE: 29

```
ggcgcccggt atttgttaaa agcggccaat aagactgaag ttgactagtc aagacgagca    60
gtccgaagcg atcgc                                                     75
```

<210> SEQ ID NO 30
<211> LENGTH: 73
<212> TYPE: DNA
<213> ORGANISM: Artificial Sequence
<220> FEATURE:
<223> OTHER INFORMATION: Amplicon 9

<400> SEQUENCE: 30

```
ggcgcccggt atttgttaaa agcggctacc tcgatcgccc atatagtcaa gacgagcagt    60
ccgaagcgat cgc                                                       73
```

<210> SEQ ID NO 31
<211> LENGTH: 75
<212> TYPE: DNA
<213> ORGANISM: Artificial Sequence
<220> FEATURE:
<223> OTHER INFORMATION: Amplicon 10

<400> SEQUENCE: 31

```
ggcgcccggt atttgttaaa agcggtgtta ggctacgata gggtttagtc aagacgagca    60
gtccgaagcg atcgc                                                     75
```

<210> SEQ ID NO 32
<211> LENGTH: 71
<212> TYPE: DNA
<213> ORGANISM: Artificial Sequence

```
<220> FEATURE:
<223> OTHER INFORMATION: Amplicon 11

<400> SEQUENCE: 32
ggcgcccggt atttgttaaa agcggtacgc gcttcatcct atagtcaaga cgagcagtcc      60
gaagcgatcg c                                                          71

<210> SEQ ID NO 33
<211> LENGTH: 74
<212> TYPE: DNA
<213> ORGANISM: Artificial Sequence
<220> FEATURE:
<223> OTHER INFORMATION: Amplicon 12

<400> SEQUENCE: 33
ggcgcccggt atttgttaaa agcggcgact catcaaacac gatttagtca agacgagcag      60
tccgaagcga tcgc                                                       74

<210> SEQ ID NO 34
<211> LENGTH: 76
<212> TYPE: DNA
<213> ORGANISM: Artificial Sequence
<220> FEATURE:
<223> OTHER INFORMATION: Amplicon 13

<400> SEQUENCE: 34
ggcgcccggt atttgttaaa agcggacaat tctcactttc gtctattagt caagacgagc      60
agtccgaagc gatcgc                                                     76

<210> SEQ ID NO 35
<211> LENGTH: 72
<212> TYPE: DNA
<213> ORGANISM: Artificial Sequence
<220> FEATURE:
<223> OTHER INFORMATION: Amplicon 14

<400> SEQUENCE: 35
ggcgcccggt atttgttaaa agcggcaccc gcatcatgta gatagtcaag acgagcagtc      60
cgaagcgatc gc                                                         72

<210> SEQ ID NO 36
<211> LENGTH: 71
<212> TYPE: DNA
<213> ORGANISM: Artificial Sequence
<220> FEATURE:
<223> OTHER INFORMATION: Amplicon 15

<400> SEQUENCE: 36
ggcgcccggt atttgttaaa agcggctcgt acgcgtggaa atagtcaaga cgagcagtcc      60
gaagcgatcg c                                                          71

<210> SEQ ID NO 37
<211> LENGTH: 75
<212> TYPE: DNA
<213> ORGANISM: Artificial Sequence
<220> FEATURE:
<223> OTHER INFORMATION: Amplicon 16

<400> SEQUENCE: 37
ggcgcccggt atttgttaaa agcggttagt caaagacgcc cgatttagtc aagacgagca      60
gtccgaagcg atcgc                                                      75
```

<210> SEQ ID NO 38
<211> LENGTH: 73
<212> TYPE: DNA
<213> ORGANISM: Artificial Sequence
<220> FEATURE:
<223> OTHER INFORMATION: Amplicon 17

<400> SEQUENCE: 38
ggcgcccggt atttgttaaa agcggtattc gcatctgggc gattagtcaa gacgagcagt    60
ccgaagcgat cgc    73

<210> SEQ ID NO 39
<211> LENGTH: 75
<212> TYPE: DNA
<213> ORGANISM: Artificial Sequence
<220> FEATURE:
<223> OTHER INFORMATION: Amplicon 18

<400> SEQUENCE: 39
ggcgcccggt atttgttaaa agcggtcctg aacttctaca tagcttagtc aagacgagca    60
gtccgaagcg atcgc    75

<210> SEQ ID NO 40
<211> LENGTH: 71
<212> TYPE: DNA
<213> ORGANISM: Artificial Sequence
<220> FEATURE:
<223> OTHER INFORMATION: Amplicon 19

<400> SEQUENCE: 40
ggcgcccggt atttgttaaa agcggactgc cagttagctg ctagtcaaga cgagcagtcc    60
gaagcgatcg c    71

<210> SEQ ID NO 41
<211> LENGTH: 73
<212> TYPE: DNA
<213> ORGANISM: Artificial Sequence
<220> FEATURE:
<223> OTHER INFORMATION: Amplicon 20

<400> SEQUENCE: 41
ggcgcccggt atttgttaaa agcggtcagt cgcaactagc gaatagtcaa gacgagcagt    60
ccgaagcgat cgc    73

<210> SEQ ID NO 42
<211> LENGTH: 74
<212> TYPE: DNA
<213> ORGANISM: Artificial Sequence
<220> FEATURE:
<223> OTHER INFORMATION: Amplicon 21

<400> SEQUENCE: 42
ggcgcccggt atttgttaaa agcggcgata gctttcgaag tacttagtca agacgagcag    60
tccgaagcga tcgc    74

<210> SEQ ID NO 43
<211> LENGTH: 19
<212> TYPE: DNA
<213> ORGANISM: Artificial Sequence
<220> FEATURE:
<223> OTHER INFORMATION: Universal forward primer

<400> SEQUENCE: 43

```
tgcaggtcaa tcccattgc                                                    19
```

<210> SEQ ID NO 44
<211> LENGTH: 24
<212> TYPE: DNA
<213> ORGANISM: Artificial Sequence
<220> FEATURE:
<223> OTHER INFORMATION: Universal reverse primer

<400> SEQUENCE: 44

```
caagcatatg aatgacctcg agaa                                              24
```

<210> SEQ ID NO 45
<211> LENGTH: 21
<212> TYPE: DNA
<213> ORGANISM: Artificial Sequence
<220> FEATURE:
<223> OTHER INFORMATION: Universal forward primer

<400> SEQUENCE: 45

```
cgcccggtat ttgttaaaag c                                                 21
```

<210> SEQ ID NO 46
<211> LENGTH: 21
<212> TYPE: DNA
<213> ORGANISM: Artificial Sequence
<220> FEATURE:
<223> OTHER INFORMATION: Universal reverse primer

<400> SEQUENCE: 46

```
cttcggactg ctcgtcttga c                                                 21
```

<210> SEQ ID NO 47
<211> LENGTH: 4233
<212> TYPE: DNA
<213> ORGANISM: Zea mays

<400> SEQUENCE: 47

```
agcctggtgt ttccggagga gacagacatg atccctgccg ttgctgatcc gacgacgctg       60
gacggcgggg gcgcgcgcag gccgttgctc ccggagacgg accctcgggg gcgtgctgcc      120
gccggcgccg agcagaagcg gccgccggct acgccgaccg ttctcaccgc cgtcgtctcc      180
gccgtgctcc tgctcgtcct cgtggcggtc acagtcctcg cgtcgcagca cgtcgacggg      240
caggctgggg gcgttcccgc gggcgaagat gccgtcgtcg tcgaggtggc cgcctcccgt      300
ggcgtggctg agggcgtgtc ggagaagtcc acggccccgc tcctcggctc cggcgcgctc      360
caggacttct cctggaccaa cgcgatgctg gcgtggcagc gcacggcgtt ccacttccag      420
ccccccaaga actggatgaa cggttagttg gacccgtcgc catcggtgac gacgcgcgga      480
tcgtttttt cttttttcct ctcgttctgg ctctaacttg gttccgcgtt tctgtcacgg      540
acgcctcgtg cacatggcga tacccgatcc gccggccgcg tatatctatc tacctcgacc      600
ggcttctcca gatccgaacg gtaagttgtt ggctccgata cgatcgatca catgtgagct      660
cggcatgctg cttttctgcg cgtgcatgcg gctcctagca ttccacgtcc acgggtcgtg      720
acatcaatgc acgatataat cgtatcggta cagagatatt gtcccatcag ctgctagctt      780
tcgcgtattg atgtcgtgac attttgcacg caggtccgct gtatcacaag ggctggtacc      840
acctcttcta ccagtggaac ccggactccg cggtatgggg caacatcacc tggggccacg      900
ccgtctcgcg cgacctcctc cactggctgc acctaccgct ggccatggtg cccgatcacc      960
```

```
cgtacgacgc caacggcgtc tggtccgggt cggcgacgcg cctgcccgac ggccggatcg    1020
tcatgctcta cacgggctcc acggcggagt cgtcggcgca ggtgcagaac ctcgcggagc    1080
cggccgacgc gtccgacccg ctgctgcggg agtgggtcaa gtcggacgcc aacccggtgc    1140
tggtgccgcc gccgggcatc gggccgacgg acttccgcga cccgacgacg gcgtgtcgga    1200
cgccggccgg caacgacacg gcgtggcggg tcgccatcgg gtccaaggac cgggaccacg    1260
cggggctggc gctggtgtac cggacggagg acttcgtgcg gtacgacccg cgcgcggcgc    1320
tgatgcacgc cgtgccgggc accggcatgt gggagtgcgt ggacttctac ccggtggccg    1380
cgggatcagg cgccgcggcg ggcagcgggg acgggctgga cgtccgcg cgcgccggga c    1440 ccggggtgaa gcacgtgctc aaggctagcc tcgacgacga caagcacgac tactacgcga    1500
tcggcaccta cgaccggcg acggacacct ggaccccga cagcgcggag gacgacgtcg      1560
ggatcggcct ccggtacgac tatggcaagt actacgcgtc gaagaccttc tacgaccccg    1620
tccttcgccg gcgggtgctc tggggtggg tcggcgagac cgacagcgag cgcgcggaca    1680
tcctcaaggg ctgggcatcc gtgcaggtac gtctcagggt ttgaggctag catggcttca    1740
atcttgctgg catcgaatca ttaatgggca gatattataa cttgataatc tgggttggtt    1800
gtgtgtggtg gggatggtga cacgcgcgcg gtaataatgt agctaagctg gttaaggatg    1860
agtaatgggg ttgcgtataa acgacagctc tgctaccatt acttctgaca cccgattgaa    1920
ggagacaaca gtaggggtag ccggtagggt tcgtcgactt gcctttctt ttttcctttg     1980 ttttgttgtg gatcgtccaa cacaaggaaa ataggatcat ccaacaaaca tggaagtaat    2040
cccgtaaaac atttctcaag gaaccatcta gctagacgag cgtggcatga tccatgcatg    2100
cacaaacact agataggtct ctgcagctgt gatgttcctt tacatatacc accgtccaaa    2160
ctgaatccgg tctgaaaatt gttcaagcag agaggcccg atcctcacac ctgtacacgt     2220
ccctgtacgc gccgtcgtgg tctcccgtga tcctgccccg tccctccac gcggccacgc     2280 ctgctgcagc gctctgtaca agcgtgcacc acgtgagaat ttccgtctac tcgagcctag    2340
tagttagacg ggaaaacgag aggaagcgca cggtccaagc acaacacttt gcgcgggccc    2400
gtgacttgtc tccggttggc tgagggcgcg cgacagagat gtatggcgcc gcggcgtgtc    2460
ttgtgtcttg tcttgcctat acaccgtagt cagagactgt gtcaaagccg tccaacgaca    2520
atgagctagg aaacggggttg gagagctggg ttcttgcctt gcctcctgtg atgtctttgc    2580
cttgcatagg gggcgcagta tgtagctttg cgttttactt cacgccaaag gatactgctg    2640
atcgtgaatt attattatta tatatatatc gaatatcgat ttcgtcgctc tcgtgggtt      2700 ttattttcca gactcaaact tttcaaaagg cctgtgtttt agttcttttc ttccaattga    2760
gtaggcaagg cgtgtgagtg tgaccaacgc atgcatggat atcgtggtag actggtagag    2820
ctgtcgttac cagcgcgatg cttgtatatg tttgcagtat tttcaaatga atgtctcagc    2880
tagcgtacag ttgaccaagt cgacgtggag ggcgcacaac agacctctga cattattcac    2940 tttttttta ccatgccgtg cacgtgcagt caatccccag gacggtcctc ctggacacga     3000
agacgggcag caacctgctc cagtggccgg tggtggaggt ggagaacctc cggatgagcg    3060
gcaagagctt cgacgcgtc gcgctggacc gcggatccgt cgtgcccctc gacgtcggca     3120
aggcgacgca ggtgacgccg cacgcagcct gctgcagcga acgaactcgc gcgttgccgg    3180
cccgcggcca gctgacttag tttctctggc tgatcgaccg tgtgcctgcg tgcgtgcagt    3240
tggacatcga ggctgtgttc gaggtggacg cgtcggacgc ggcgggcgtc acggaggccg    3300
acgtgacgtt caactgcagc accagcgcag gcgcggcggg ccggggcctg ctcggcccgt    3360
```

| | |
|---|---|
| tcggccttct cgtgctggcg gacgacgact tgtccgagca gaccgccgtg tacttctacc | 3420 |
| tgctcaaggg cacggacggc agcctccaaa ctttcttctg ccaagacgag ctcaggtatg | 3480 |
| tatgttatga cttatgacca tgcatgcatg cgcatttctt agctaggctg tgaagcttct | 3540 |
| tgttgagttg tttcacagat gcttaccgtc tgctttgttt cgtatttcga ctaggcatcc | 3600 |
| aaggcgaacg atctggttaa gagagtatac gggagcttgg tccctgtgct agatggggag | 3660 |
| aatctctcgg tcagaatact ggtaagtttt tacagcgcca gccatgcatg tgttggccag | 3720 |
| ccagctgctg gtactttgga cactcgttct tctcgcactg ctcattattg cttctgatct | 3780 |
| ggatgcacta caaattgaag gttgaccact ccatcgtgga gagctttgct caaggcggga | 3840 |
| ggacgtgcat cacgtcgcga gtgtacccca cacgagccat ctacgactcc gcccgcgtct | 3900 |
| tcctcttcaa caacgccaca catgctcacg tcaaagcaaa atccgtcaag atctggcagc | 3960 |
| tcaactccgc ctacatccgg ccatatccgg caacgacgac ttctctatga ctaaattaag | 4020 |
| tgacggacag ataggcgata ttgcatactt gcatcatgaa ctcatttgta caacagtgat | 4080 |
| tgtttaattt atttgctgcc ttccttatcc ttcttgtgaa actatatggt acacacatgt | 4140 |
| atcattaggt ctagtagtgt tgttgcaaag acacttagac accagaggtt ccaggagtat | 4200 |
| cagagataag gtataagagg gagcagggag cag | 4233 |

<210> SEQ ID NO 48
<211> LENGTH: 2480
<212> TYPE: DNA
<213> ORGANISM: Zea mays

<400> SEQUENCE: 48

| | |
|---|---|
| gcggccgcct ggtaggcgct ggtacaagcg gaagcagcag tagcgtgagg catccccatg | 60 |
| ccgggggcaa tctcttcctc gtcgtcggct tttctcctcc ccgtcgcgtc ctcctcgccg | 120 |
| cggcgcaggc ggggcagtgt gggtgctgct ctgcgctcgt acggctacag cggcgcggag | 180 |
| ctgcggttgc attgggcgcg gcggggcccg cctcaggatg gagcggcgtc ggtacgcgcc | 240 |
| gcagcggcac cggccggggg cgaaagcgag gaggcagcga agagctcctc ctcgtcccag | 300 |
| gcgggcgctg ttcagggcag cacggccaag gctgtggatt ctgcttcacc tcccaatcct | 360 |
| ttgacatctg ctccgaagca aagtcagagc gctgcaatgc aaaacggaac gagtgggggc | 420 |
| agcagcgcga gcaccgccgc gccggtgtcc ggacccaaag ctgatcatcc atcagctcct | 480 |
| gtcaccaaga gagaaatcga tgccagtgcg gtgaagccag agcccgcagg tgatgatgct | 540 |
| agaccggtgg aaagcatagg catcgctgaa ccggtggatg ctaaggctga tgcagctccg | 600 |
| gctacagatg cggcggcgag tgctccttat gacagggagg ataatgaacc tggccctttg | 660 |
| gctgggccta atgtgatgaa cgtcgtcgtg gtggcttctg aatgtgctcc tttctgcaag | 720 |
| acaggtggcc ttggagatgt cgtgggtgct ttgcctaagg ctctggcgag gagaggacac | 780 |
| cgtgttatgg tcgtgatacc aagatatgga gagtatgccg aagcccggga tttaggtgta | 840 |
| aggagacgtt acaaggtagc tggacaggat tcagaagtta cttatttca ctcttacatt | 900 |
| gatggagttg atttgtatt cgtagaagcc cctcccttcc ggcaccggca caataatatt | 960 |
| tatggggag aaagattgga tattttgaag cgcatgattt tgttctgcaa ggccgctgtt | 1020 |
| gaggttccat ggtatgctcc atgtggcggt actgtctatg gtgatggcaa cttagttttc | 1080 |
| attgctaatg attggcatac cgcacttctg cctgtctatc taaaggccta ttaccgggac | 1140 |
| aatggtttga tgcagtatgc tcgctctgtg cttgtgatac acaacattgc tcatcagggt | 1200 |

```
cgtggccctg tagacgactt cgtcaatttt gacttgcctg aacactacat cgaccacttc    1260
aaactgtatg acaacattgg tggggatcac agcaacgttt ttgctgcggg gctgaagacg    1320
gcagaccggg tggtgaccgt tagcaatggc tacatgtggg agctgaagac ttcggaaggc    1380
gggtggggcc tccacgacat cataaaccag aacgactgga agctgcaggg catcgtgaac    1440
ggcatcgaca tgagcgagtg gaaccccgct gtggacgtgc acctccactc cgacgactac    1500
accaactaca cgttcgagac gctggacacc ggcaagcggc agtgcaaggc cgccctgcag    1560
cggcagctgg gcctgcaggt ccgcgacgac gtgccactga tcgggttcat cgggcggctg    1620
gaccaccaga agggcgtgga catcatcgcc gacgcgatcc actggatcgc ggggcaggac    1680
gtgcagctcg tgatgctggg caccgggcgg gccgacctgg aggacatgct gcggcggttc    1740
gagtcggagc acagcgacaa ggtgcgcgcg tgggtggggt tctcggtgcc cctggcgcac    1800
cgcatcacgg cgggcgcgga catcctgctg atgccgtcgc ggttcgagcc gtgcgggctg    1860
aaccagctct acgccatggc gtacgggacc gtgcccgtgg tgcacgccgt gggggggctc    1920
cgggacacgg tggcgccgtt cgacccgttc aacgacaccg ggctcgggtg gacgttcgac    1980
cgcgcggagg cgaaccggat gatcgacgcg ctctcgcact gcctcaccac gtaccggaac    2040
tacaaggaga gctggcgcgc ctgcagggcg cgcggcatgg ccgaggacct cagctgggac    2100
cacgccgccg tgctgtatga ggacgtgctc gtcaaggcga agtaccagtg gtgagcgaat    2160
taattggcga cgcgacgccg ctcctgtcgc aggacctgga cgttatttag aaggctcttc    2220
tccctggcgg ctttgatgcg tgcgtcgcat ttgcgccggg cggacgggcg acggtggttg    2280
gcctaccgcc tacgtcggct gcgtgccctg ggaatttggg cgggcacgat gatgccactg    2340
ggcaccgggc gcggggtagt atgatatgaa accgacggcg atggagatga ggcgcatggc    2400
attttcccac tgataaatgg ggagttgtat gctactttaa tatcgccact cctgttagta    2460
tttatattga tggcggccgc                                                 2480
```

<210> SEQ ID NO 49
<211> LENGTH: 18
<212> TYPE: DNA
<213> ORGANISM: Artificial Sequence
<220> FEATURE:
<223> OTHER INFORMATION: Forward invertase primer

<400> SEQUENCE: 49
tggcggacga cgacttgt                                                   18

<210> SEQ ID NO 50
<211> LENGTH: 19
<212> TYPE: DNA
<213> ORGANISM: Artificial Sequence
<220> FEATURE:
<223> OTHER INFORMATION: Reverse invertase primer

<400> SEQUENCE: 50
aaagtttgga ggctgccgt                                                  19

<210> SEQ ID NO 51
<211> LENGTH: 26
<212> TYPE: DNA
<213> ORGANISM: Artificial Sequence
<220> FEATURE:
<223> OTHER INFORMATION: Invertase probe oligonucleotide

<400> SEQUENCE: 51
cgagcagacc gccgtgtact tctacc                                          26

<210> SEQ ID NO 52
<211> LENGTH: 22
<212> TYPE: DNA
<213> ORGANISM: Artificial Sequence
<220> FEATURE:
<223> OTHER INFORMATION: Forward ZSSIIb primer

<400> SEQUENCE: 52
ctcccaatcc tttgacatct gc                                            22

<210> SEQ ID NO 53
<211> LENGTH: 23
<212> TYPE: DNA
<213> ORGANISM: Artificial Sequence
<220> FEATURE:
<223> OTHER INFORMATION: Reverse ZSSIIb primer

<400> SEQUENCE: 53
tcgatttctc tcttggtgac agg                                           23

<210> SEQ ID NO 54
<211> LENGTH: 25
<212> TYPE: DNA
<213> ORGANISM: Artificial Sequence
<220> FEATURE:
<223> OTHER INFORMATION: ZSSIIb probe oligonucleotide

<400> SEQUENCE: 54
agcaaagtca gagcgctgca atgca                                         25

<210> SEQ ID NO 55
<211> LENGTH: 84
<212> TYPE: DNA
<213> ORGANISM: Artificial Sequence
<220> FEATURE:
<223> OTHER INFORMATION: Polynucleotide comprising unique genetic
      element and flanking universal primer sites

<400> SEQUENCE: 55
ggcgcctgca ggtcaatccc attgcttttg ttcaattctg gaaatcctct ctgcgatcgc   60
ttctcgaggt cattcatatg cttg                                          84

<210> SEQ ID NO 56
<211> LENGTH: 86
<212> TYPE: DNA
<213> ORGANISM: Artificial Sequence
<220> FEATURE:
<223> OTHER INFORMATION: Polynucleotide comprising unique genetic
      element and flanking universal primer sites

<400> SEQUENCE: 56
ggcgcctgca ggtcaatccc attgcttttg attggtttgg tggtgagatt ctctgcgatc   60
gcttctcgag gtcattcata tgcttg                                        86

<210> SEQ ID NO 57
<211> LENGTH: 83
<212> TYPE: DNA
<213> ORGANISM: Artificial Sequence
<220> FEATURE:
<223> OTHER INFORMATION: Polynucleotide comprising unique genetic
      element and flanking universal primer sites

<400> SEQUENCE: 57
ggcgcctgca ggtcaatccc attgcttttg aacaaaggcc ccaatctctc tgcgatcgct   60

```
tctcgaggtc attcatatgc ttg                                          83

<210> SEQ ID NO 58
<211> LENGTH: 84
<212> TYPE: DNA
<213> ORGANISM: Artificial Sequence
<220> FEATURE:
<223> OTHER INFORMATION: Polynucleotide comprising unique genetic
      element and flanking universal primer sites

<400> SEQUENCE: 58
ggcgcctgca ggtcaatccc attgcttttg cacctaccca ccctacttct ctgcgatcgc    60
ttctcgaggt cattcatatg cttg                                          84

<210> SEQ ID NO 59
<211> LENGTH: 85
<212> TYPE: DNA
<213> ORGANISM: Artificial Sequence
<220> FEATURE:
<223> OTHER INFORMATION: Polynucleotide comprising unique genetic
      element and flanking universal primer sites

<400> SEQUENCE: 59
ggcgcctgca ggtcaatccc attgcttttg cgttatcccg catagtagtc tctgcgatcg    60
cttctcgagg tcattcatat gcttg                                         85

<210> SEQ ID NO 60
<211> LENGTH: 85
<212> TYPE: DNA
<213> ORGANISM: Artificial Sequence
<220> FEATURE:
<223> OTHER INFORMATION: Polynucleotide comprising unique genetic
      element and flanking universal primer sites

<400> SEQUENCE: 60
ggcgcctgca ggtcaatccc attgcttttg acgtatcaca gctcctagtc tctgcgatcg    60
cttctcgagg tcattcatat gcttg                                         85
```